United States Patent
Lizarzaburu Chavez et al.

(10) Patent No.: US 11,591,611 B2
(45) Date of Patent: Feb. 28, 2023

(54) TOLCNDV RESISTANT MELON PLANTS

(71) Applicant: NUNHEMS B.V., Nunhem (NL)

(72) Inventors: Juan Antonio Lizarzaburu Chavez, Cartagena-Murcia (ES); Jeffrey Skoneczka, Davis, CA (US); Daniel Bellon Doña, Cartagena (ES)

(73) Assignee: NUNHEMS B.V., Nunhem (NL)

( * ) Notice: Subject to any disclaimer, the term of this patent is extended or adjusted under 35 U.S.C. 154(b) by 196 days.

(21) Appl. No.: 17/155,700

(22) Filed: Jan. 22, 2021

(65) Prior Publication Data

US 2021/0163980 A1 Jun. 3, 2021

Related U.S. Application Data

(63) Continuation-in-part of application No. 16/317,496, filed as application No. PCT/EP2017/067078 on Jul. 7, 2017, now Pat. No. 10,947,557.

(60) Provisional application No. 62/500,941, filed on May 3, 2017.

(30) Foreign Application Priority Data

Jul. 12, 2016 (EP) .................................. 16179134

(51) Int. Cl.
| | | |
|---|---|---|
| *C12N 15/82* | (2006.01) | |
| *A01H 1/04* | (2006.01) | |
| *A01H 6/34* | (2018.01) | |
| *A01H 1/00* | (2006.01) | |
| *A01H 5/08* | (2018.01) | |

(52) U.S. Cl.
CPC ......... *C12N 15/8283* (2013.01); *A01H 1/045* (2021.01); *A01H 1/126* (2021.01); *A01H 5/08* (2013.01); *A01H 6/344* (2018.05)

(58) Field of Classification Search
None
See application file for complete search history.

(56) References Cited

FOREIGN PATENT DOCUMENTS

| WO | 2010123904 A1 | 10/2010 |
| WO | 2014090968 A1 | 6/2014 |
| WO | 2017114848 A1 | 7/2017 |

OTHER PUBLICATIONS

Fauquet, C. M., et al., "Geminivirus strain demarcation and nomenclature", Archives of Virology; vol. 153, No. 4, Feb. 7, 2008, pp. 783-821.
López, C., et al., "Mechanical transmission of Tomato leaf curl New Delhi virus to cucurbit germplasm: selection of tolerance sources in Cucumis melo", EUPHYTICA, vol. 204, No. 3, Jan. 28, 2015, pp. 679-691.
Allen, A.M., et al., "Transcript-specific, single-nucleotide polymorphism discovery and linkage analysis in hexapioid bread wheat (*Triticum aestivum* L.)," Plant Biotechnology Journal, vol. 9, 2011, pp. 1086-1099.
Argyris, J.M, et al., "Use of targeted SNP selection for an improved anchoring of the melon (*Cucumis melo* L.) scaffold genome assembly," BMC Genomics, vol. 16, No. 4, 2015, pp. 1-14.
Diaz, A., et al., "Anchoring the consensus ICuGI genetic map to the melon (*Cucumis melo* L.) genome," Mol. Breeding, vol. 35, No. 188, 2015, pp. 1-7.
EPPO Reporting Service: "European and Mediterranean Plant Protection Organization", Jun. 1, 2015, pp. 1-21, Paris Retrieved from the Internet: URL:http://archives.eppo.int/EPPOReporting/2015/Rse-1506.pdf—[retrieved on Mar. 11, 2016].
Garcia-Mas, J., et al., "The genome of melon (*Cucumis melo* L.)", PNAS, vol. 109, No. 29, Jul. 17, 2012, pp. 11872-11877.
Henikoff, S., et al., "Amino acid substitution matrices from protein blocks," PNAS, vol. 89, Nov. 1992, pp. 10915-10919.
Islam, S., et al., "Genetics of resistance in Luffa cylindrica Roem. against Tomato leaf curl New Delhi virus," Feb. 12, 2010, Euphytica , vol. 174, No. 1, pp. 83-89.
Saez et al., "Resistance to Tomato leaf curl New Delhi virus in *Cucurbita* spp.," Annals of Applied Biology, vol. 169, 2016, pp. 91-105.
Saez, C., et al., "Inheritance of Tolerance to Tomato Leaf Curl New Dehli Virus (ToLCNDV) in Melon," (Proceedings of Cucurbitaeceae 2016, the XIth EUCARPIA Meeting on Genetics and Breeding of Cucurbitaceae Jul. 24-28, 2016) Jul. 2016, pp. 214-216.
Varma, A., et al., "GE Tomato Resistant to Leaf Curl Disease," Jun. 2006, ISB News Report, pp. 1-3.
Yazdani-Khameneh, S., et al., "Report of a new begomovirus on melon in Iran," New Disease Reports, vol. 28, Dec. 19, 2013, p. 17.
International Search Report issued in PCT/EP2017/067078, dated Sep. 8, 2017, pp. 1-5.

*Primary Examiner* — Elizabeth F McElwain
(74) *Attorney, Agent, or Firm* — ArentFox Schiff LLP

(57) ABSTRACT

The application concerns melon plants (*Cucumis melo*) resistant to infection with tomato leaf curl New Dehli virus (ToLCNDV). The resistant melon plants have a genomic introgression fragment on chromosome 5 which confers tolerance to ToLCNDV in a dominant manner. Also disclosed are markers for identifying those fragments, methods for identifying or producing resistant melon plants.

13 Claims, 2 Drawing Sheets

Specification includes a Sequence Listing.

TOLCNDV RESISTANT MELON PLANTS

CROSS-REFERENCE TO RELATED APPLICATIONS

This application is a continuation-in-part of U.S. patent application Ser. No. 16/317,496, filed on Jan. 11, 2019, which is a 35 U.S.C. 371 National Phase of PCT Application No. PCT/EP2017/067078, filed on Jul. 7, 2017, which claims priority to EP Application No. 16179134.8, filed Jul. 12, 2016, and U.S. Patent Application No. 62/500,941, filed May 3, 2017, the disclosures of which are hereby incorporated by reference in their entireties.

FIELD

The application concerns melon plants (*Cucumis melo*) resistant to infection with tomato leaf curl New Dehli virus (ToLCNDV). The resistant melon plants have a genomic introgression fragment on chromosome 5 which confers tolerance to ToLCNDV in a dominant manner. Also disclosed are markers for identifying those fragments, methods for identifying or producing resistant melon plants.

BACKGROUND

Tomato leaf curl New Dehli virus (ToLCNDV) is classified as Begomovirus belonging to the family Geminiviridae. ToLCNDV has a bipartite genome consisting of two single stranded DNA molecules referred to as DNA A and DNA B (Saez et al., 2016, Annals of Applied Biology).

ToLCNDV was initially found to infect tomato (*Solanum lycopersicum*) plants in 1995 in India. Later ToLCNDV was found to infect also plants of other Solanacea species, like *Solanum melongena* (aubergine), chili pepper (*Capsicum* spp.) and *Solanum tuberosum* (potato). In 2012 infection of curcubit species (courgette, *Cucurbita pepo* var. *giromontiina*) by ToLCNDV was found in Spain and in 2015 the virus was identified as the disease source in melon, cucumber and courgette in Tunisia. In the meantime, infection of many Curcubitacea species such as *Benincasa hispida* (wax gourd), *Citrullus lanatus* (watermelon), *Cucumis melo* (melon), *Cucumis melo* var. *flexuosus* (snake melon), *Cucumis sativus* (cucumber), *Cucurbita moschata* (musky gourd), *Cucurbita pepo* (pumpkin), *Cucurbita pepo* var. *giromontiina* (courgette), *Lagenaria siceraria* (bottle gourd), *Luffa cylindrica* (sponge gourd), *Momordica charantia* (bitter gourd) have been proven. Infection of weeds (e.g. *Eclipta prostrata*—Asteraceae) and other crops such as *Hibiscus cannabinus* (kenaf—Malvaceae) and *Carica papaya* (papaya—Caricaceae) was also reported. In the Mediterranean region the disease does occur in various crop species in Italy (Sicilia), Spain and Tunisia. In Asian countries, infection was proven in different crops in Bangladesh, India, Indonesia, Pakistan, Philippines, Sri Lanka, Taiwan and Thailand. Further information on geographical distribution of ToLCNDV is lacking, but from the observations made today, the virus clearly seems to further spread geographically as well as to other crops. Disease symptoms in general comprise phenotypic appearance of yellow mosaic on leaves, leaf curling, vein swelling, and plant stunting. Cucurbits upon infection of young plants with ToLCNDV show stunted growth and decreased or suppressed fruit production. Also fruits showing skin roughness and longitudinal cracking have been reported. Thus, ToLCNDV causes economic losses in various important crop species and is a major threat. Infection of plants by ToLCNDV occurs persistently by transmission of the virus by the phloem sucking whitefly (*Bemisia tabaci*). (European and Mediterranean Plant Protection Organization, EPPO RS 2015/114, 2016/024, 2016/040, Entry date 2015-06).

In sponge gourd resistance to ToLCNDV has been shown to be controlled by a single dominant gene (Islam et al., 2010, Euphytica 174(1):83-89).

In tomato, transgenic plants resistant to ToLCNDV have been produced by silencing virus genes (Varma & Praveen, 2006, ISB News Report).

Assays for transmission of ToLCNDV by mechanically transferring the sap of an infected zucchini plant to non-infected plants from other cucurbit genera (*Cucumis, Cucurbita, Citrullus, Lagenaria*) have been developed. Five *Cucumis melo* accessions (subsp. *agrestis* var. *momordica*: Mom-KhaInd/Kharbuja, Mom-PI124Ind/PI 124112, Mom-PI124Ind/PI 414723 and subsp. *agrestis* wild types: Ag-WM9Ind/WM9, Ag-WM7Ind/WM7) resistant to ToLCNDV were identified (Lopez et al., 2015, Euphytica 204(3), 679-691). Confirmation of resistance of these accessions by using the natural whitefly infection system was not performed.

Saez et al. 2016, pages 214-216 (Proceedings of Cucurbitaeceae 2016, the XIth EUCARPIA Meeting on Genetics and Breeding of Cucurbitaceae Jul. 24-28, 2016, Warsaw, Poland) describe that ToLCNDV resistance of the *C. melo* subsp. *agrestis* accession WM-7 segregated in an F2 population in a 3:1 ratio of tolerant: susceptible, suggesting a single dominant resistance gene being present in WM-7. As in Lopez et al. 2015, supra, mechanical inoculation was used, and not natural infection via whitefly vector.

Various *Cucurbita* species (*C. pepo, C. moschata, C. maxima, C. fraternal, C. ficifolia*) have been screened for resistance to ToLCNDV by the mechanical sap transmission screening assay. Four *Curcurbita moschata* accessions (PI 604506, PI 381814, Nigerian local, Kurokawa) were found to show low symptoms upon, mechanical infection with ToLCNDV. This result however could be reproduced upon whitefly infection only for two of the accession (PI 604506, PI 381814), demonstrating that resistance to ToLCNDV should be tested not only under artificial conditions but in addition by using the naturally occurring whitefly infection system (Saez et al., 2016, Annals of Applied Biology). Therefore, it is unclear if the accessions identified to be resistant to infection by ToLCNDV are resistant under natural growing conditions when the virus is transferred by whiteflies.

Attempts to control ToLCNDV infection of crop plants comprise vector (whitefly) control by insecticides applications and adaption of cultural practices, including use of virus free crop material (transplants), establishment of crop free periods, weed management (eliminating virus infected weeds) and destruction of infected plants in the field. However, because of the complex epidemiological factors associated with the disease, these attempts are not always effective (Saez et al., 2016, Annals of Applied Biology).

Therefore, there is a need to establish further measurements for reducing ToLCNDV infections, further spreading of the virus to other geographical areas and spreading to other crop species. Breeding of varieties resistant to ToLCNDV would be essential for managing the disease.

SUMMARY OF VARIOUS EMBODIMENTS

An object of the present invention is to provide measurements for the control of ToLCNDV infection in melon plants.

The present invention discloses melon plant cells and melon plants being resistant to infections by ToLCNDV.

DETAILED DESCRIPTION OF VARIOUS EMBODIMENTS

It is commonly known that ToLCNDV does infect various different plant species of the Curcubitaceae species, including melon species. It is also well known that ToLCNDV is transmitted persistently from infected plants to non-infected plants by the plant sucking pest *Bemisia tabaci* (whitefly). Transfer of ToLCNDV from one crop species to different crop species or even from weed species to crop species has been demonstrated. Whiteflies may pick up ToLCNDV from outside the controlled area even from different species and transfer it to melon plants grown in the controlled area. Whitefly vector control therefore is of limited effectiveness for preventing ToLCNDV infection. ToLCNDV resistant melon plants have the advantage that they would withstand infection with ToLCNDV without major yield losses, even if plants around the area where the melon plants are grown are infected with ToLCNDV.

The inventors found a ToLCNDV resistant donor accession of melon and have mapped the resistance in a segregating population, using whitefly infection with a Spanish ToLCNDV strain for resistance phenotyping. A Quantitative Trait Locus (QTL) was identified on chromosome 5 (QTL5) and introgressed from the wild donor accession into an elite cultivated melon line. Seeds of the elite line, comprising the QTL5 introgression in homozygous form, were deposited by Nunhems B.V. under Accession number NCIMB 42585 in accordance with the Budapest Treaty. In these seeds the donor genotype for the Single Nucleotide Polymorphism (SNP) markers (SNP_01 to SNP_08) provided herein is present. The donor itself is not uniform and has white fruit flesh with a low brix. It is not an accession of agronomic value. The donor is also not available anymore at the US seed bank. By identifying and transferring QTL5 from the donor into cultivated melon, it is now possible to make cultivated melon varieties and cultivars of high agronomic value (with uniform characteristics and marketable fruits having high brix and good shelf life) with resistance against ToLCNDV and thus it is possible to cultivate those melon varieties in ToLCNDV infested areas without yield loss.

"Melon plant cells" or "melon plants" also designated as muskmelon plant cells or muskmelon plants in the art shall be understood in context with the present invention to be plant cells originating from the species *Cucumis melo* or to be plants belonging to the species *Cucumis melo*.

*Cucumis melo*, can be classified into: *C. melo cantalupensis*, *C. melo inodorous* and *C. melo reticulatus*. *C. melo cantalupensis* are also referred to as Cantaloupes and are primarily round in shape with prominent ribs and almost no netting. Most have orange, sweet flesh and they are usually very fragrant. In contrast to the European cantaloupe, the North American 'Cantaloupe' is not of this type, but belongs to the true muskmelons. *C. melo inodorous* (or winter melons) can be subdivided into different types, such as Honeydew melon, Piel de Sapo, Sugar melon, Japanese melon, etc. *C. melo reticulatus* is the true muskmelon, with reticulated skin (netted) and includes Galia melons, Sharlyn melons and the North American cantaloupe.

Melon and the wild relatives of melon is/are diploid and has/have 12 pairs of homologous chromosomes, numbered 1 to 12.

"Resistant" or "being resistant to" shall be understood in context of the present invention to mean a plant which is a host species of a particular pathogen and can therefore be infected by a given pathogen, but wherein the plant comprises a genetic element (e.g. an introgression fragment) resulting in reduction of pathogen growth and/or spreading in the plant after infection compared to the susceptible plant lacking the genetic element. In context of the present invention "resistant" or "being resistant to" in particular refers to plant cells or plants being resistant to ToLCNDV. Resistance is a relative term which can span a range of (different) reactions in the plant cell or plant, triggered by pathogen infection. The effect of those reactions by the plant cell or plant can be measured by various means. Typically the effect is measured by defining a symptom level appearing in the plant cell or plant. Typically average symptoms of several plants of a line (e.g. 10 or more) are compared to average symptoms of several plants of a control line or variety, preferably a susceptible control line or variety. Thus at least 10 or more individual plants of a line or variety are scored at one time point and the average disease score is calculated.

Concerning the present invention, the following commonly known symptom levels are applied according to phenotypic observations taken after ToLCNDV infection:

1=Dead plant

2=Severe mosaic and curling, chlorosis and growth reduction. No recovery

3=Strong mosaic and curling, chlorosis and growth reduction. No recovery

4=Curling and mosaic, chlorosis, no or mild growth reduction. No recovery

5=Curling and mosaic, chlorosis, no growth reduction. Slight recovery of the upper plant zone 6=Mild curling, mosaic and chlorosis, no growth reduction. Recovery of the upper middle plant 7=Mild curling, mosaic and chlorosis, no growth reduction. Symptoms appear only in the lower plant zone 8=Faint mosaic 9=No symptoms For determining the symptom level (or disease score) preferably young plants are infected with ToLCNDV. Young plants are preferably plants having the age of the first true leaf being expanded, preferably approximately 12-15 days after sowing. Infection is preferably carried out via feeding of the vector (*Bemisia*) carrying the virus. For this purpose plants are germinated and grown under optimal or close to optimal conditions. The symptom level is preferably determined at least once, e.g. 30 days after infection (or later, e.g. 31, 32, 33, 34, 35 days after infection). Optionally symptom level is determined twice or even three times at different time-points following infection to confirm the result, e.g. a first scoring at approximately 15, 20 or 25 days after infection and a second scoring at approximately 30 days after infection (or later, e.g. 31, 32, 33, 34, 35 days after infection) with ToLCNDV. See also the Examples. In one aspect a plant line is said to be resistant against ToLCNDV infection if it has an average disease score of 5.0 or higher, while the susceptible control line or variety, such as variety Gandalf (or Gandalf F1, Nunhems B.V.) or Vedantrais, has an average disease score of 2.5 or less, or 2.0 or less, when grown under the same conditions and infected in the same way.

It has been observed that introgression of a specific fragment located on chromosome 5 in a wild melon donor plant into cultivated melon plants confers resistance to ToLCNDV infection in cultivated melon plants or cells derived therefrom. It is sufficient that the respective fragment is present only in the heterozygous state for conferring ToLCNDV resistance, demonstrating that the fragment confers resistance to ToLCNDV infection in a dominant manner. Single Nucleotide Polymorphisms (SNPs) on chromosome 5 were identified which are closely linked to the fragment of chromosome 5 conferring ToLCNDV resistance. The SNP nucleotide of the resistant donor (i.e. the nucleotide of the introgression fragment) is present in homozygous form in the deposited seeds, i.e. the donor nucleotide is present in homozygous form for SNP_01 to SNP_08 (linked to QTL5). The SNPs can, therefore, be used to test the presence of the introgression fragment comprising the QTL5 in a plant cell, plant tissue, plant part, and/or in marker assisted selection (MAS) to transfer the QTLs into other elite melon lines or varieties. The SNPs can also be used to select plants comprising smaller introgressions fragments than the fragments present in the deposited seeds, whereby the smaller sub-fragments retain the QTL. Alternatively the SNPs can be used to identify other donors which comprise QTL5 and to introgress these QTLs into cultivated melon.

The present invention therefore relates to melon plant cells or melon plants comprising an introgression fragment from chromosome 5 of a ToLCNDV resistant donor plant, wherein the introgression fragment comprises the sequence of the donor plant in-between SNP_01 and SNP_06, preferably the sequence of the donor plant in-between SNP_01 and SNP_05, more preferably the sequence of the donor plant in-between SNP_01 and SNP_04. The ToLCNDV resistance conferring QTL is present on the introgression fragment, as can be determined by a resistance assay as described herein.

In a preferred embodiment the present invention relates to cultivated melon plant cells or melon plants comprising an introgression fragment from chromosome 5 of a ToLCNDV resistant donor plant, wherein the introgression fragment comprises the sequence of the donor plant in-between SNP_02 and SNP_06, preferably the sequence of the donor plant in-between SNP_02 and SNP_05, more preferably the sequence of the donor melon plant in-between SNP_02 and SNP_04.

The present invention further relates to melon plant cells or melon plants comprising an introgression fragment from chromosome 5 of a ToLCNDV resistant donor plant, wherein the introgression fragment comprises the sequence of the ToLCNDV resistant donor plant in-between SNP_03 and SNP_06, preferably the sequence of the ToLCNDV resistant donor plant in-between SNP_03 and SNP_05.

Most preferred, the present invention relates to melon plant cells or melon plants comprising an introgression fragment from chromosome 5 of a ToLCNDV resistant donor plant, wherein the introgression fragment comprises the sequence of the ToLCNDV resistant donor melon plant in-between SNP_03 and SNP_04.

The ToLCNDV resistance conferring QTL has been further fine-mapped to be located in between SNP_03 and SNP_04 and to be closely linked to SNP_07 and/or SNP_08, which are located in between SNP_03 and SNP_04 on chromosome 5. Therefore, the present invention relates to melon plant cells or melon plants comprising an introgression fragment from chromosome 5 of a ToLCNDV resistant donor plant, wherein the introgression fragment comprises the sequence of the ToLCNDV resistant donor melon plant in-between SNP_03 and SNP_04 and comprises the donor SNP nucleotide (i.e. a Cytosine) for SNP_07 at nucleotide 101 of SEQ ID NO: 25 and/or comprises the donor SNP nucleotide (i.e. a Guanine) for SNP_08 at nucleotide 101 of SEQ ID NO: 26.

In another aspect, the present invention relates to melon plant cells or melon plants comprising an introgression fragment from chromosome 5 of a ToLCNDV resistant donor plant, wherein the introgression fragment comprises the sequence of the ToLCNDV resistant donor melon plant in-between SNP_07 and SNP_08 and comprises the donor SNP nucleotide (i.e. a Cytosine) for SNP_07 at nucleotide 101 of SEQ ID NO: 25 and/or comprises the donor SNP nucleotide (i.e. a Guanine) for SNP_08 at nucleotide 101 of SEQ ID NO: 26.

When referring herein to the introgression fragment comprising the sequence "in-between" two SNPs (Single Nucleotide Polymorphisms), this encompasses in one aspect that one or both of the two SNPs themselves are also from the resistant donor, i.e. have the donor nucleotide at the SNP position. In another aspect, the two SNPs are from the recipient, e.g. the susceptible melon plant, while only a region between the two SNPs is from the resistant donor and confers ToLCNDV resistance, i.e. the resistance conferring donor fragment lies in-between the two SNP markers. So for example, a plant may comprise the introgression fragment comprising the sequence of the ToLCNDV resistant donor melon plant in-between SNP_03 and SNP_04, this plant in one aspect comprises a Thymine (T) at nucleotide 68 of SEQ ID NO: 3 and/or an Adenine (A) at nucleotide 227 of SEQ ID NO: 4, i.e. the donor nucleotides. In another aspect only a region (the whole region or a part thereof) between these two SNPs is from the donor, while SNP_03 and SNP_04 are from the recipient, having e.g. a Cytosine (C) at nucleotide 68 of SEQ ID NO: 3 and e.g. a Guanine (G) at nucleotide 227 of SEQ ID NO: 4.

Thus, regarding the QTL on chromosome 5, SNP_01, SNP_02, SNP_03, SNP_07, SNP_08, SNP_04, SNP_05 and SNP_06 may all have the resistant donor genotype. Or only SNP_01 and SNP_02 may have the resistant donor genotype; or only SNP_02 and SNP_03 may have the resistant donor genotype; or only SNP_03 and SNP_04, or only SNP_07 and SNP_08, may have the resistant donor genotype, etc. Or only a single SNP, i.e. only SNP_01, or only SNP_02 or only SNP_03, or only SNP_04, or only SNP_05 or only SNP_06, or only SNP_07 or only SNP_08 has the resistant donor genotype. The SNPs that do not have the resistant donor genotype thus have another genotype, the recipient genotype. The recipient genotype for a SNP may be any of the other 3 nucleotides, i.e. for SNP_01 the recipient genotype may be Adenine, Guanine or Thymine. Thus, for example when stating that the introgression fragment is in-between SNP_03 and SNP_04 regarding the QTL on chromosome 5, SNP_03 and SNP_04 may both have the resistant donor genotype. Or only a single SNP, i.e. only SNP_03 or only SNP_04 may have the resistant donor genotype; or even neither SNP_03 nor SNP_04 has the resistant donor genotype, while the sequence in-between still contains QTL5.

The reason that not all of the SNPs provided herein need to have the resistant donor genotype is that the introgression fragment comprising the QTL from the donor may be smaller than the chromosome fragment introgressed e.g. in the deposited seeds, but the fragment still comprises the QTL5. Still, a plant can be recognized to contain the introgression fragment (comprising the QTL5) by the phenotype, and/or by transferring the fragment to a susceptible plant and thereby transferring the ToLCNDV resistance phenotype, or by sequencing the region between the SNP markers to identify the donor fragment, or other methods known to the skilled person, such as saturating the region with more SNP markers, allelism tests, identifying the causal gene, etc.

Thus, a combination of methods can be used to show that the QTL5 is present in a plant cell or plant, even if not for all of the linked SNPs the donor SNP genotype is present. QTL5 confers an average ToLCNDV resistance of at least 5.0 when transferred into a susceptible line or variety and is dominant.

In a preferred embodiment of the invention, the introgression fragment from chromosome 5 of the donor plant comprising the sequence of the donor plant in-between SNP_01 and SNP_06, in-between SNP_01 and SNP_05, in-between SNP_01 and SNP_04, in-between SNP_02 and SNP_06, in-between SNP_02 and SNP_05, in-between SNP_02 and SNP_04, in-between SNP_03 and SNP_06, in-between SNP_03 and SNP_05, preferably in-between SNP_03 and SNP_04 confers resistance to ToLCNDV to the cultivated melon plant cells according to the invention or to the cultivated melon plants according to the invention.

As the resistance was fine mapped to be located in-between SNP_03 and SNP_04, with two new markers being present in this region which are closely linked to the resistance, SNP_07 and SNP_08, it is an aspect herein that the introgression fragment comprises the donor sequence in between SNP_03 and SNP_04 and comprises the donor nucleotide for SNP_07 and/or SNP_08; or in-between SNP_07 and SNP_08 and comprises the donor nucleotide for SNP_07 and/or SNP_08, or in-between SNP_03 and SNP_08 and comprises the donor nucleotide for SNP_07 and/or SNP_08, or in-between SNP_08 and SNP_04 and comprises the donor nucleotide for SNP_07 and/or SNP_08, or in-between SNP_07 and SNP_04 and comprises the donor nucleotide for SNP_07 and/or SNP_08.

Preferably, the melon plant cell according to the invention originates from a cultivated melon plant or the melon plant according to the invention, is a cultivated melon plant.

In one aspect the present invention, relates to cultivated melon plant cells or melon plants (or plant parts) comprising an introgression fragment from chromosome 5 of a ToLCNDV resistant donor plant, wherein the introgression fragment confers ToLCNDV resistance and the introgression fragment is detectable by (comprises) the SNP genotype of the donor plant for one or more (or all) of the following SNPs: SNP_01, SNP_02, SNP_03, SNP_07, SNP_08, SNP_04, SNP_05 and/or SNP_06, and optionally any SNP in-between SNP_01 and SNP_06.

In one aspect the plant, plant part or plant cell comprises QTL5 and comprises the SNP donor genotype for at least SNP_03, as this SNP is significantly associated with the ToLCNDV resistance QTL5. In a further aspect the plant, plant part or plant cell comprises the SNP donor genotype for at least SNP_03 and SNP_04, or for at least SNP_03 and SNP_02. Optionally, the plant, plant part or plant cell comprises QTL5 and comprises the SNP donor genotype for SNP_01, SNP_02 and SNP_03; or for SNP_02, SNP_03 and SNP_04.

In one aspect, the plant, plant part or plant cell comprises QTL5 and comprises the SNP donor genotype for at least SNP_07 or SNP_08, as these SNPs are most significantly associated with the ToLCNDV resistance QTL5. In a further aspect, the plant, plant part or plant cell comprises the SNP donor genotype for at least SNP_07 and SNP_08, or for at least SNP_03 and SNP_07, or for at least SNP_08 and SNP_04. Optionally, the plant, plant part or plant cell comprises QTL5 and comprises the SNP donor genotype for SNP_03, SNP_07 and SNP_08; or for SNP_07, SNP_08 and SNP_04.

An introgression fragment may therefore comprise the donor SNP genotype for all SNP markers linked to QTL5 (as in the seeds deposited herein), or a smaller fragment, whereby one or more of the SNP markers is not present. As described further below, even all or all but one donor SNP markers may be absent, while QTL5 is still present on the introgression fragment.

The nucleotide sequences (SEQ ID NO: 1 to SEQ ID NO: 6, and SEQ ID NO: 25 comprising SNP_07 and SEQ ID NO: 26 comprising SNP_08) comprising the SNPs provided herein are the nucleotide sequences of the resistant donor, i.e. they contain the donor SNP nucleotide. Therefore, in one aspect the present invention relates to cultivated melon plant cells or melon plants (or plant parts) comprising an introgression fragment from chromosome 5 of a ToLCNDV resistant donor plant, wherein the introgression fragment confers ToLCNDV resistance and the introgression fragment is detectable by (comprises) SEQ ID NO: 1 or an Cytosine at nucleotide 101 of SEQ ID NO: 1 (or a Guanine at nucleotide 101 in the complementary strand of SEQ ID NO: 1) or a Cytosine at the equivalent nucleotide of a sequence having substantial sequence identity to SEQ ID NO: 1 and/or by SEQ ID NO: 2 or a Thymine at nucleotide 945 of SEQ ID NO: 2 or a Thymine at the equivalent nucleotide of a sequence having substantial sequence identity to SEQ ID NO:2 and/or by SEQ ID NO: 3 or a Thymine at nucleotide 68 of SEQ ID NO: 3 or a Thymine at the equivalent nucleotide of a sequence having substantial sequence identity to SEQ ID NO: 3, and/or by SEQ ID NO: 25 or a Cytosine at nucleotide 101 of SEQ ID NO: 25 (or a Guanine at nucleotide 101 in the complementary strand of SEQ ID NO: 25) or a Cytosine at the equivalent nucleotide of a sequence having substantial sequence identity to SEQ ID NO: 25 and/or by SEQ ID NO: 26 or a Guanine at nucleotide 101 of SEQ ID NO: 26 (or a Cytosine at nucleotide 101 in the complementary strand of SEQ ID NO: 26) or a Guanine at the equivalent nucleotide of a sequence comprising substantial sequence identity to SEQ ID NO: 26, and/or by SEQ ID NO: 4 or a Adenine at nucleotide 227 of SEQ ID NO: 4 or a Adenine at the equivalent nucleotide of a sequence having substantial sequence identity to SEQ ID NO: 4 and/or by SEQ ID NO: 5 or a Cytosine at nucleotide 839 of SEQ ID NO: 5 (or a Guanine at nucleotide 839 in the complementary strand of SEQ ID NO: 5) or a Cytosine at the equivalent nucleotide of a sequence having substantial sequence identity to SEQ ID NO: 5 and/or by SEQ ID NO: 6 or a Adenine at nucleotide 445 of SEQ ID NO: 6 or a Adenine at the equivalent nucleotide of a sequence having substantial sequence identity to SEQ ID NO: 6. The ToLCNDV resistance conferring QTL is present on the introgression fragment.

The sequences provided herein for SEQ ID NO: 1 (comprising SNP_01), SEQ ID NO: 5 (comprising SNP_05), SEQ ID NO: 25 (comprising SNP_07) and SEQ ID NO: 26 (comprising SNP_08) are (−) strand/reverse strand sequences of the double stranded DNA of chromosome 5 when comparing these sequences to the sequence orientation given for the reference genome of melon. Therefore, another way to refer to the sequences and the SNP nucleotide is to refer to the (+) strand/forward strand, which is the complement nucleotide or sequence of the (−) strand. Thus, SNP_01 is a Cytosine at nucleotide 101 of SEQ ID NO: 1 or a Guanine at nucleotide 101 of the complementary strand of SEQ ID NO: 1.

"Donor plant cell" or "donor plant" in connection with the present invention shall mean a melon plant cell or melon plant being resistant to ToLCNDV. Likewise, the term DNA fragment or introgression fragment from the donor plant or cell shall mean a fragment of chromosome 5 of a melon plant resistant to ToLCNDV, whereby the fragment confers ToLCNDV resistance when transferred into a TolCNDV susceptible melon plant. In a preferred embodiment of the invention, the donor plant is a wild species or wild accession of melon. In a particular preferred embodiment of the invention, DNA fragments or introgression fragments from donor plant cells or plants are the donor fragments obtained from plants grown from seeds deposited under NCIMB 42585 or progeny obtained from plants grown from seeds deposited under NCIMB 42585 or plants obtained by crosses with plants grown from seeds deposited under NCIMB 42585.

Donor melon plants can be obtained from various sources. A person skilled in the art knows how to detect other sources of ToLCNDV resistant donor plants. For detecting such sources of ToLCNDV resistant donor plants, basically melon plants can be infected with ToLCNDV, either by mechanical means, as described in Lopez et al. (2015, Euphytica 204(3), 679-691) or by transmission of the virus by whiteflies. Preferably, infection occurs by whitefly infection in context with the present invention. Plants showing reduced symptom levels compared to susceptible controls can then be selected and used as source for genome fragments or sequences conferring ToLCNDV resistance. A preferred method on how to infect melon plants with ToLCNDV and methods for determining the symptom level of infected plants are given herein under "General Methods".

In context of the present invention, the donor plants preferably have an average symptom level equal to or above 5.0, more preferably equal to or above 6.0, furthermore preferred equal to or above 7.0, even more preferred equal to or above 8.0 and most preferred equal to or above 9.0. In one aspect the donor plant comprises the donor SNP genotype for one or more or all of SNP_01, SNP_2, SNP_3, SNP_04, SNP_05, SNP_06, SNP_07 and SNP_08, as shown in Table 2 and Table 3. Preferably, the SNP donor genotype is homozygous. The donor is herein e.g. a wild melon having no agronomic value, e.g. producing white fleshed fruits, having low brix, etc.

"Recurrent plant cell" or "recurrent plant" or "recipient plant" in connection with the present invention shall be understood to be a melon plant cell or melon plant being sensitive (used herein synonymously with susceptible) or non-resistant to ToLCNDV infection. If a plant is sensitive or non-resistant to ToLCNDV can be determined by observation of the symptom levels after ToLCNDV infection. A recurrent plant preferably has an average symptom level below 3.0, more preferably equal to or below 2.5 or equal to or below 2.0. Symptom levels and methods how to infect melon plants with ToLCNDV are described elsewhere herein and are applicable here accordingly. In a preferred embodiment of the invention, the recurrent melon plant cell according to the invention originates from a cultivated melon plant or the recurrent melon plant according to the invention, is a cultivated melon plant. Preferably it is an elite line, breeding line or variety.

"Introgression fragment" refers to a chromosome fragment, chromosome part or region which has been introduced into another plant of the same or related species by crossing or traditional breeding techniques. The introgression of the fragment from a donor plant into a recurrent plant introduces into the offspring of a cross between the donor and recurrent plant a phenotype, which was not present in the recurrent plant. Concerning the present invention, the phenotype transferred from the donor plant to the recurrent plant is resistance to ToLCNDV, e.g. an average disease score of 5.0. For introgression of a fragment into a specific breeding line or variety the first crossing step can e.g. be followed by one or more backcrossings with the intended breeding line or variety. As understood herein, introgression can mean a first crossing of a ToLCNDV resistant donor plant with a ToLCNDV non-resistant recurrent plant and further backcrossing one or several times ToLCNDV resistant plants obtained from the first crossing with plants of the recipient into which ToLCNDV resistance shall be introgressed. In such a case, the introgressed fragment is the result of breeding methods referred to by the verb "to introgress" (such as backcrossing) into a recipient variety or breeding line. Thus, introgression of ToLCNDV resistance into a recurrent plant is a technical process directed by man. In particular introgression herein refers to a manmade breeding process or method. One or more or all of the molecular markers (SNP markers) provided herein can be used in that process. The resulting plant, i.e. the cultivated line or variety comprising one introgression fragment (on chromosome 5) from a donor, i.e. comprising a recombinant chromosome 5, is also man-made and does not exist in nature.

The introgression fragment can be large, e.g. even half of a chromosome, but is preferably smaller, such as about 15 Mb or less, such as about 10 Mb or less, about 9 Mb or less, about 8 Mb or less, about 7 Mb or less, about 6 Mb or less, about 5 Mb or less, about 4 Mb or less, about 3 Mb or less, about 2 Mb or less, about 1 Mb (equals 1,000,000 base or less), or about 0.8 Mb (equals 800,000 base pairs) or less.

The introgression fragment can originate from a wild melon plant or wild melon accession or wild relatives of melon or landraces (donor). Wild melon plants or wild melon accessions or wild relatives of melon plants or landraces can be used to introgress fragments of the donor genome into the genome of cultivated melon, *Cucumis melo*, to generate breeding lines or varieties with good agronomic characteristics. Such a cultivated melon plant thus has a "genome of cultivated *C. melo*", but comprises in its genome a fragment of a donor, e.g. an introgression fragment of a related wild *Cucumis* genome, such as *Cucumis melo* ssp. *agrestis, C. melo* ssp. *melo, C. melo* ssp. a *cidulous, C. callosus, C. trigonus, C. picrocarpus*, or another wild melon or wild relative of melon. It is understood that the term "introgression fragment" never includes a whole chromosome, but only a part of a chromosome. The chromosomes carrying the introgression therefore also comprise a part or parts of the recurrent (recipient) melon plant and in addition parts of the donor melon plant.

When the chromosome 5 of cultivated melon comprises an introgression fragment, this therefore means that the cultivated melon plant comprises a recombinant chromosome 5, whereby the introgressed fragment comprises the ToLCNDV resistance conferring QTL. As described elsewhere, the introgression fragment from the donor may comprise one or more or all of the donor SNP nucleotides (for SNP_01, SNP_02, SNP_03, SNP_04, SNP_05, SNP_06, SNP_07 and/or SNP_08) or one or more or all of the sequences comprising the donor SNP nucleotides (SEQ ID NO: 1, 2, 3, 4, 5, 6, 25 and/or SEQ ID NO: 26).

So, e.g. the introgression fragment (in homozygous or heterozygous form) may comprise, and is detectable by, one or more or all of the following SNP genotypes: the CC or CT genotype for SNP_01 in SEQ ID NO: 1, and/or the TT or TG genotype for SNP_02 in SEQ ID NO: 2, and/or the TT or TC genotype for the SNP_03 in SEQ ID NO: 3, and/or the CC or CT genotype for SNP_07 in SEQ ID NO: 25, and/or the GG or GA genotype for SNP_08 in SEQ ID NO: 26, and/or the AA or AG genotype for the SNP_04 in SEQ ID NO: 4, and/or the CC or CT genotype for SNP_05 in SEQ ID NO: 5, and/or the AA or AG genotype for SNP_06 in SEQ ID NO: 6.

In the instant invention, in one aspect the lower part of chromosome 5 of cultivated melon, below marker CMGAAN144 on chromosome 5 on page 3 of Diaz et al 2015 (Mol. Breeding 35: 188), or between marker CMGAAN144 and marker AI_13-H12, comprises QTL5 from a donor.

In one aspect the donor plant of the invention is not one of the five *Cucumis melo* subsp.*agrestis* accessions (subsp. *agrestis* var. *momordica*: Mom-KhaInd/Kharbuja, Mom-PI124Ind/PI124112, Mom-PI124Ind/PI414723 and subsp. *agrestis* wild types: Ag-WM9Ind/WM9, Ag-WM7Ind/WM7) resistant to ToLCNDV identified by Lopez et al., 2015, Euphytica 204(3), 679-691. In one aspect the donor plant of the invention is not of the species *Cucumis melo* subsp. *agrestis*.

The term "breeding" encompasses herein crossing, backcrossing, selfing, selection, double haploid production, embryo rescue, protoplast fusion, marker assisted selection, mutation breeding etc. as known to the breeder (i.e. methods other than genetic modification/transformation/transgenic methods), by which, for example, a recombinant chromosome 5 can be obtained, identified, produced and/or transferred.

In a preferred embodiment of the present invention, the introgression fragment originates form a wild *Cucumis* plant or a wild *Cucumis* accession, most preferably the introgression fragment originates from wild *Cucumis melo* ssp. *melo*, having small fruits (no more than 6 cm long), with white, acid tasting, fruit flesh. This donor was used in the instant invention, but other donors can be identified by the skilled person which comprise e.g. the same SNP genotype as this donor for SNP_01 to SNP_08 and comprises a QTL in the same region of chromosome 6.

A suitable donor is in one aspect a wild *C. melo* plant or accession having an average ToLCNDV disease score of at least 7.0, or at least 7.1, 7.2, 7.3, or 7.4 or 7.5 or 7.6, on a scale of 1=dead plant to 9=no symptoms and comprises one or more or all of the following SNP genotypes: the CC or CT genotype for SNP_01 in SEQ ID NO: 1, and/or the TT or TG genotype for SNP_02 in SEQ ID NO: 2, and/or the TT or TC genotype for the SNP_03 in SEQ ID NO: 3, and/or the CC or CT genotype for SNP_07 in SEQ ID NO: 25, and/or the GG or GA genotype for SNP_08 in SEQ ID NO: 26, and/or the AA or AG genotype for the SNP_04 in SEQ ID NO: 4, and/or the CC or CT genotype for SNP_05 in SEQ ID NO: 5, and/or the AA or AG genotype for SNP_06 in SEQ ID NO: 6.

"Plant variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of one or two loci or genes (or phenotypic characteristics due to these specific loci or genes), but which can otherwise differ from one another enormously as regards the other loci or genes.

"F1, F2, F3, etc." refers to the consecutive related generations following a cross between two parent plants or parent lines. The plants grown from the seeds produced by crossing two plants or lines is called the F1 generation. Selfing the F1 plants results in the F2 generation, etc.

"F1 hybrid" plant (or F1 hybrid seed) is the generation obtained from crossing two inbred parent lines. Thus, F1 hybrid seeds are seeds from which F1 hybrid plants grow. F1 hybrids are more vigorous and higher yielding, due to heterosis. Inbred lines are essentially homozygous at most loci in the genome.

A "plant line" or "breeding line" refers to a plant and its progeny. As used herein, the term "inbred line" refers to a plant line which has been repeatedly selfed and is nearly homozygous. Thus, an "inbred line" or "parent line" refers to a plant which has undergone several generations (e.g. at least 5, 6, 7 or more) of inbreeding, resulting in a plant line with a high uniformity.

"Uniformity" or "uniform" relates to the genetic and phenotypic characteristics of a plant line or variety. Inbred lines are genetically highly uniform as they are produced by several generations of inbreeding. Likewise, and the F1 hybrids which are produced from such inbred lines are highly uniform in their genotypic and phenotypic characteristics and performance.

In a particular preferred embodiment of the invention, plant cells according to the invention and plants according to the invention are characterized in that the introgression fragment conferring ToLCNDV resistance originates from the seeds deposited under NCIMB 42585 or progeny thereof.

In a further preferred embodiment of the invention, the melon plant cell according to the invention originates from a cultivated melon plant or the melon plant according to the invention is a cultivated melon plant and the introgression fragment originates form a wild *Cucumis* plant or a wild *Cucumis* accession or from donor plants described herein to be preferred donor plants or obtained from seeds deposited under NCIMB 42585 or progeny thereof.

"Chromosome 5 of a melon plant" is to be understood in context of the present invention as the scaffolds, fragments, regions, markers and nucleic acid sequences assigned by the ICuGI (International Cucurbit Genomics Initiative) to belong to chromosome 5 of the melon genome. The ICuGI website is now the cucurbitgenomics.org website and chromosome 5 of a melon plant corresponds to chromosome 5 of the reference melon genome in the database, e.g. melon DHL92.

"Orthologous chromosome 5" refers to the chromosome 5 of wild relatives of melon, parts of which can be introgressed into cultivated melon chromosome 5.

A "recombinant chromosome" refers to a chromosome having a new genetic makeup arising through crossing over between homologous chromosomes, e.g. a "recombinant chromosome 5", i.e. a chromosome 5 which is not present in either of the parent plants and arose through a rare crossing-over event between homologous chromosomes of a chromosome 5 pair. Herein, for example, a recombinant melon chromosome 5 comprising a ToLCNDV-resistance conferring QTL is provided. The recombinant chromosome 5 therefore is a chromosome of cultivated melon, with an introgression fragment from a wild donor, whereby the introgression fragment comprises the ToLCNDV resistance conferring QTL.

"ICuGI" refers herein to the *Cucumis melo* data published by the International Cucurbit Genomics Initiative, which publishes genetic maps of e.g. *Cucumis melo* (world wide web at icugi.org/cgi-bin/ cmap/mapset_info?species acc=CM, which is now found at cucurbitgenomics.org). The version CM_3.5.1 of the *C. melo* genome map is of Mar. 4, 2012 and the map of chromosome 5 is referred to as ICuGI_V (or LG_V, or Linkage Group V). Further information including additional markers and mapping information in addition to the ICuCI data is available from Diaz et al. (2015, Mol Breeding 35, 188) and the additional data included in the online version of the respective article.

"Cultivated melon plant" refers to plants of *Cucumis melo* i.e. varieties, breeding lines or cultivars of the species *C. melo*, cultivated by humans and having good agronomic characteristics, especially producing edible and marketable fruits of good size and quality and uniformity; such plants are not "wild melon plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of a species.

A "SNP (=Single Nucleotide Polymorphism)" in context with the present invention is to be understood as a variation in a single nucleotide that occurs at a specific position in the genome. A SNP is the variation of the single nucleotide at the given position in a genome between two plants. If a wild melon plant having a ToLCNDV resistance (donor plant) shows in its corresponding sequence at a specific single position a nucleotide which is different from the corresponding nucleotide at the same position of a cultivated melon plant, the position defines a SNP between the wild melon and the cultivated melon. If the donor plant has one of the four possible nucleotides (A, C, T or G) at a specific position, a SNP occurs, when the cultivated plant has either of the remaining three possible nucleotides at the same corresponding sequence position. In a cultivated melon plant comprising an introgression fragment from a donor, it can therefore easily be determined if the single nucleotide of the SNP is from the donor or from the cultivated melon (recipient).

'SNP nucleotide' refers to the single nucleotide, while 'SNP genotype' refers to the pair of nucleotides in a diploid plant cell. So, for SNP_01, the SNP nucleotide of the ToLCNDV resistant donor is a Cytosine (C) for nucleotide 101 of SEQ ID NO: 1, while the SNP genotype of a plant or cell comprising SEQ ID NO: 1 can be CC (Cytosine on both chromosomes) or CT (Cytosine on one chromosome and Thymine on the other chromosome), whereby the ToLCNDV resistant donor SNP nucleotide (Cytosine), and thus SEQ ID NO: 1 (or a sequence substantially identical to SEQ ID NO: 1), is homozygous or heterozygous. The term "SNP donor genotype" refers to the donor SNP nucleotide being present in homozygous or in heterozygous form, i.e. for SNP_01 the SNP donor genotype is either CC or CT.

"SNP_01" which is alternatively designated "mME11320_k" is to be understood in context with the present invention to be a SNP at position 101 in SEQ ID NO 1. SEQ ID NO 1 or a sequence substantially identical to SEQ ID NO 1 can be found on chromosome 5 e.g. in the ICuGI data set or in the reference genome of melon as shown in Table 3. The relative position of SNP_01 according to markers published by ICuGI is derivable from Table 1. Preferably the nucleotide sequence comprising SNP_01 has a nucleotide sequence having at least 85% identity with the nucleotide sequence shown under SEQ ID NO 1, more preferably at least 90%, 91%, 92%, 93%, 94% identity with the nucleotide sequence shown under SEQ ID NO 1, further more preferably at least 95% identity with the nucleotide sequence shown under SEQ ID NO 1, even more preferred at least 97% identity with the nucleotide sequence shown under SEQ ID NO 1, even further more preferred at least 98% identity with the nucleotide sequence shown under SEQ ID NO 1, in particular preferred at least 99% identity with the nucleotide sequence shown under SEQ ID NO 1 or more particularly preferred at least 99.5% identity with the nucleotide sequence shown under SEQ ID NO 1 under the provision that in each case the nucleotide at position 101 in SEQ ID NO 1 is different from the corresponding nucleotide at the same position of the recurrent plant. Such sequences having at least 85%, 90%, 91%, 92%, 93%, 94%, 95%, 97%, 98%, 99% or more sequence identity to SEQ ID NO: 1 are referred to as having substantial sequence identity to SEQ ID NO: 1.

The ToLCNDV resistant donor plants used in the invention have a 'C'(Cytosine) at position 101 in SEQ ID NO 1 or in a sequence comprising substantial sequence identity to SEQ ID NO:1. In a preferred embodiment of the invention, SNP_01 is characterized in that the recurrent plant has an A, G or T at position 101 in SEQ ID NO 1. In one aspect, the recurrent plant has a T at position 101 in SEQ ID NO 1.

In one embodiment of the invention, SNP_01 is characterized in that the donor plant has a C at position 101 of SEQ ID NO 1 (or at the equivalent position of a sequence comprising substantial sequence identity to SEQ ID NO: 1) and the recurrent plant has a T at position 101 in SEQ ID NO 1.

As SEQ ID NO: 1 corresponds to the (−) strand of the double stranded DNA of each chromosome 5, an alternative way of referring to SNP_01 is to refer to the SNP at position 101 of the complementary strand of SEQ ID NO: 1. The ToLCNDV resistant donor plant has a 'G' (Guanine) at position 101 of the complementary strand of SEQ ID NO: 1 or in a sequence comprising substantial sequence identity to the complementary strand of SEQ ID NO: 1.

In one embodiment of the invention, SNP_01 is characterized in that the donor plant has a G at position 101 of the complementary strand of SEQ ID NO 1 (or at the equivalent position of a sequence comprising substantial sequence identity to the complementary strand of SEQ ID NO: 1) and the recurrent plant has an A at position 101 of the complementary strand of SEQ ID NO 1.

"SNP_02" which is alternatively designated "mME43070_k" is to be understood in context with the present invention to be a SNP at position 945 in SEQ ID NO 2. SEQ ID NO 2 or a sequence substantially identical to SEQ ID NO 2 can be found on chromosome 5 e.g. in the ICuGI data set or in the reference genome of melon as shown in Table 3. The relative position of SNP_02 according to markers published by ICuGI is derivable from Table 1. Preferably the nucleotide sequence comprising SNP_02 has a nucleotide sequence having at least 85% identity with the nucleotide sequence shown under SEQ ID NO 2, more preferably at least 90%, 91%, 92%, 93%, 94% identity with the nucleotide sequence shown under SEQ ID NO 2, further more preferably at least 95% identity with the nucleotide sequence shown under SEQ ID NO 2, even more preferred at least 97% identity with the nucleotide sequence shown under SEQ ID NO 2, even further more preferred at least 98% identity with the nucleotide sequence shown under SEQ ID NO 2, in particular preferred at least 99% identity with the nucleotide sequence shown under SEQ ID NO 2 or more particularly preferred at least 99.5% identity with the nucleotide sequence shown under SEQ ID NO 2 under the provision that in each case the nucleotide at position 945 in SEQ ID NO 2 is different from the corresponding nucleotide at the same position of the recurrent plant. Such sequences having at least 85%, 90%, 91%, 92%, 93%, 94%, 95%, 97%, 98%, 99% or more sequence identity to SEQ ID NO 2 are referred to as having substantial sequence identity to SEQ ID NO: 2.

The ToLCNDV resistant donor plants used in the invention have a 'T' (Thymine) at position 945 in SEQ ID NO 2 or in a sequence comprising substantial sequence identity to SEQ ID NO: 2.

In one embodiment of the invention, SNP_02 is characterized in that the recurrent plant has an A, C or G at position 945 in SEQ ID NO 2 or in a sequence comprising substantial sequence identity to SEQ ID NO: 2.

In one aspect, the recurrent plant has a 'G' (Guanine) at position 945 in SEQ ID NO 2 or in a sequence comprising substantial sequence identity to SEQ ID NO: 2.

In a particular embodiment of the invention, SNP_02 is characterized in that the donor plant has a T at position 945 in SEQ ID NO 2 (or in a sequence comprising substantial sequence identity to SEQ ID NO: 2) and the recurrent plant has a G at position 945 in SEQ ID NO 2 (or in a sequence comprising substantial sequence identity to SEQ ID NO: 2).

"SNP_03" which is alternatively designated "mME10621_k" is to be understood in context with the present invention to be a SNP at position 68 in SEQ ID NO 3. SEQ ID NO 3 or a sequence substantially identical to SEQ ID NO 3 can be found on chromosome 5 e.g. in the ICuGI data set or in the reference genome of melon as shown in Table 3. The relative position of SNP_03 according to markers published by ICuGI is derivable from Table 1. Preferably the nucleotide sequence comprising SNP_03 has a nucleotide sequence having at least 85% identity with the nucleotide sequence shown under SEQ ID NO 3, more preferably at least 90%, 91%, 92%, 93%, 94% identity with the nucleotide sequence shown under SEQ ID NO 3, further more preferably at least 95% identity with the nucleotide sequence shown under SEQ ID NO 3, even more preferred at least 97% identity with the nucleotide sequence shown under SEQ ID NO 3, even further more preferred at least 98% identity with the nucleotide sequence shown under SEQ ID NO 3, in particular preferred at least 99% identity with the nucleotide sequence shown under SEQ ID NO 3 or more particularly preferred at least 99.5% identity with the nucleotide sequence shown under SEQ ID NO 3 under the provision that in each case the nucleotide at position 68 in SEQ ID NO 3 is different from the corresponding nucleotide at the same position of the recurrent plant. Such sequences having at least 85%, 90%, 91%, 92%, 93%, 94%, 95%, 97%, 98%, 99% or more sequence identity to SEQ ID NO 3 are referred to as having substantial sequence identity to SEQ ID NO: 3.

The ToLCNDV resistant donor plants used in the invention have a 'T' (Thymine) at position 68 in SEQ ID NO 3 (or in a sequence comprising substantial sequence identity to SEQ ID NO: 3). In one embodiment of the invention, SNP_03 is characterized in that the recurrent plant has an A, C or G at position 68 in SEQ ID NO 3 (or in a sequence comprising substantial sequence identity to SEQ ID NO: 3). In one aspect the recurrent plant has a C position 68 in SEQ ID NO 3 (or in a sequence comprising substantial sequence identity to SEQ ID NO: 3).

In one embodiment of the invention, SNP_03 is characterized in that the donor plant has a 'T' at position 68 in SEQ ID NO 3 (or in a sequence comprising substantial sequence identity to SEQ ID NO: 3) and the recurrent plant has a 'C' at position 68 in SEQ ID NO 3 (or in a sequence comprising substantial sequence identity to SEQ ID NO: 3).

"SNP_04" which is alternatively designated "mME50729_k" is to be understood in context with the present invention to be a SNP at position 227 in SEQ ID NO 4. SEQ ID NO 4 or a sequence substantially identical to SEQ ID NO 4 can be found on chromosome 5 e.g. in the ICuGI data set or in the reference genome of melon as shown in Table 3. The relative position of SNP_04 according to markers published by ICuGI is derivable from Table 1. Preferably the nucleotide sequence comprising SNP_04 has a nucleotide sequence having at least 85% identity with the nucleotide sequence shown under SEQ ID NO 4, more preferably at least 90%, 91%, 92%, 93%, 94% identity with the nucleotide sequence shown under SEQ ID NO 4, further more preferably at least 95% identity with the nucleotide sequence shown under SEQ ID NO 4, even more preferred at least 97% identity with the nucleotide sequence shown under SEQ ID NO 4, even further more preferred at least 98% identity with the nucleotide sequence shown under SEQ ID NO 4, in particular preferred at least 99% identity with the nucleotide sequence shown under SEQ ID NO 4 or more particularly preferred at least 99.5% identity with the nucleotide sequence shown under SEQ ID NO 4 under the provision that in each case the nucleotide at position 227 in SEQ ID NO 4 is different from the corresponding nucleotide at the same position of the recurrent plant. Such sequences having at least 85%, 90%, 91%, 92%, 93%, 94%, 95%, 97%, 98%, 99% or more sequence identity to SEQ ID NO 4 are referred to as having substantial sequence identity to SEQ ID NO: 4.

The ToLCNDV resistant donor plants used in the invention have an 'A' (Adenine) at position 227 in SEQ ID NO 4 (or in a sequence comprising substantial sequence identity to SEQ ID NO: 4). In one embodiment of the invention, SNP_04 is characterized in that the recurrent plant has an C, T or G at position 227 in SEQ ID NO 4 (or in a sequence comprising substantial sequence identity to SEQ ID NO: 4). In one aspect the recurrent plant has a G position 227 in SEQ ID NO 4 (or in a sequence comprising substantial sequence identity to SEQ ID NO: 4).

In one embodiment of the invention, SNP_04 is characterized in that the ToLCNDV resistant donor plant has an A at position 227 in SEQ ID NO 4 (or in a sequence comprising substantial sequence identity to SEQ ID NO: 4) and the recurrent plant has a G at position 227 in SEQ ID NO 4 (or in a sequence comprising substantial sequence identity to SEQ ID NO: 4).

"SNP_05" which is alternatively designated "mME32395_k" is to be understood in context with the present invention to be a SNP at position 839 in SEQ ID NO 5. SEQ ID NO 5 or a sequence substantially identical to SEQ ID NO 5 can be found on chromosome 5 e.g. in the ICuGI data set or in the reference genome of melon as shown in Table 3. The relative position of SNP_05 according to markers published by ICuGI is derivable from Table 1. Preferably the nucleotide sequence comprising SNP_05 has a nucleotide sequence having at least 85% identity with the nucleotide sequence shown under SEQ ID NO 5, more preferably at least 90%, 91%, 92%, 93%, 94% identity with the nucleotide sequence shown under SEQ ID NO 5, further more preferably at least 95% identity with the nucleotide sequence shown under SEQ ID NO 5, even more preferred at least 97% identity with the nucleotide sequence shown under SEQ ID NO 5, even further more preferred at least 98% identity with the nucleotide sequence shown under SEQ ID NO 5, in particular preferred at least 99% identity with the nucleotide sequence shown under SEQ ID NO 5 or more particularly preferred at least 99.5% identity with the nucleotide sequence shown under SEQ ID NO 5 under the provision that in each case the nucleotide at position 839 in SEQ ID NO 5 is different from the corresponding nucleotide at the same position of the recurrent plant. Such sequences having at least 85%, 90%, 91%, 92%, 93%, 94%, 95%, 97%, 98%, 99% or more sequence identity to SEQ ID NO 5 are referred to as having substantial sequence identity to SEQ ID NO: 5.

The ToLCNDV resistant donor plants used in the invention have a 'C' (Cytosine) at position 839 in SEQ ID NO 5 (or in a sequence comprising substantial sequence identity to SEQ ID NO: 5). In one embodiment of the invention, SNP_05 is characterized in that the recurrent plant has an A, T or G at position 839 in SEQ ID NO 5 (or in a sequence comprising substantial sequence identity to SEQ ID NO: 5). In one aspect the recurrent plant has a T position 839 in SEQ ID NO 5 (or in a sequence comprising substantial sequence identity to SEQ ID NO: 5).

In one embodiment of the invention, SNP_05 is characterized in that the ToLCNDV resistant donor plant has a C at position 839 in SEQ ID NO 5 (or in a sequence comprising substantial sequence identity to SEQ ID NO: 5) and the recurrent plant has a T at position 839 in SEQ ID NO 5 (or in a sequence comprising substantial sequence identity to SEQ ID NO: 5).

As SEQ ID NO: 5 corresponds to the (−) strand of the double stranded DNA of each chromosome 5, an alternative way of referring to SNP_05 is to refer to the SNP at position 839 of the complementary strand of SEQ ID NO: 5. The ToLCNDV resistant donor plant has a 'G' (Guanine) at position 839 of the complementary strand of SEQ ID NO 5 or in a sequence comprising substantial sequence identity to the complementary strand of SEQ ID NO: 5.

In one embodiment of the invention, SNP_05 is characterized in that the donor plant has a G at position 839 of the complementary strand of SEQ ID NO 5 (or at the equivalent position of a sequence comprising substantial sequence identity to the complementary strand of SEQ ID NO: 5) and the recurrent plant has an A at position 839 of the complementary strand of SEQ ID NO 5.

"SNP_06" which is alternatively designated "mME49184_k" is to be understood in context with the present invention to be a SNP at position 445 in SEQ ID NO 6. SEQ ID NO 6 or a sequence substantially identical to SEQ ID NO 6 can be found on chromosome 5 e.g. in the ICuGI data set or in the reference genome of melon as shown in Table 3. The relative position of SNP_06 according to markers published by ICuGI is derivable from Table 1. Preferably the nucleotide sequence comprising SNP_06 has a nucleotide sequence having at least 85% identity with the nucleotide sequence shown under SEQ ID NO 6, more preferably at least 90%, 91%, 92%, 93%, 94% identity with the nucleotide sequence shown under SEQ ID NO 6, further more preferably at least 95% identity with the nucleotide sequence shown under SEQ ID NO 6, even more preferred at least 97% identity with the nucleotide sequence shown under SEQ ID NO 6, even further more preferred at least 98% identity with the nucleotide sequence shown under SEQ ID NO 6, in particular preferred at least 99% identity with the nucleotide sequence shown under SEQ ID NO 6 or more particularly preferred at least 99.5% identity with the nucleotide sequence shown under SEQ ID NO 6 under the provision that in each case the nucleotide at position 445 in SEQ ID NO 6 is different from the corresponding nucleotide at the same position of the recurrent plant. Such sequences having at least 85%, 90%, 91%, 92%, 93%, 94%, 95%, 97%, 98%, 99% or more sequence identity to SEQ ID NO 6 are referred to as having substantial sequence identity to SEQ ID NO: 6.

The ToLCNDV resistant donor plants used in the invention have an 'A' (Adenine) at position 445 in SEQ ID NO 6 (or in a sequence comprising substantial sequence identity to SEQ ID NO: 6). In one embodiment of the invention, SNP_06 is characterized in that the recurrent plant has a C, T or G at position 445 in SEQ ID NO 6 (or in a sequence comprising substantial sequence identity to SEQ ID NO: 6). In one aspect the recurrent plant has a G position 445 in SEQ ID NO 6 (or in a sequence comprising substantial sequence identity to SEQ ID NO: 6).

In a particular embodiment of the invention, SNP_06 is characterized in that the ToLCNDV resistant donor plant has an A at position 445 in SEQ ID NO 6 (or in a sequence comprising substantial sequence identity to SEQ ID NO: 6) and the recurrent plant has a G at position 445 in SEQ ID NO 6 (or in a sequence comprising substantial sequence identity to SEQ ID NO: 6).

"SNP_07" which is alternatively designated "mME72207" is to be understood in context with the present invention to be a SNP at position 101 in SEQ ID NO 25. SEQ ID NO 25 or a sequence substantially identical to SEQ ID NO 25 can be found on chromosome 5. The position of SNP_07 on the chromosome of the reference genome is given in Table 3. Preferably, the nucleotide sequence comprising SNP_07 has a nucleotide sequence having at least 85% identity with the nucleotide sequence shown under SEQ ID NO 25, more preferably at least 90%, 91%, 92%, 93%, 94%, identity with the nucleotide sequence shown under SEQ ID NO 25, further more preferably at least 95% identity with the nucleotide sequence shown under SEQ ID NO 25, even more preferred at least 97% identity with the nucleotide sequence shown under SEQ ID NO 25, even further more preferred at least 98% identity with the nucleotide sequence shown under SEQ ID NO 25, in particular preferred at least 99% identity with the nucleotide sequence shown under SEQ ID NO 25 or more particularly preferred at least 99.5% identity with the nucleotide sequence shown under SEQ ID NO 25 under the provision that in each case the nucleotide at position 101 in SEQ ID NO 25 is different from the corresponding nucleotide at the same position of the recurrent plant. Such sequences having at least 85%, 90%, 91%, 92%, 93%, 94%, 95%, 97%, 98%, 99% or more sequence identity to SEQ ID NO 25 are referred to as having substantial sequence identity to SEQ ID NO: 25.

The ToLCNDV resistant donor plants used in the invention have a 'C' (Cytosine) at position 101 in SEQ ID NO 25 (or in a sequence comprising substantial sequence identity to SEQ ID NO: 25). In one embodiment of the invention, SNP_07 is characterized in that the recurrent plant has an A, T or G at position 101 in SEQ ID NO 25 (or in a sequence comprising substantial sequence identity to SEQ ID NO: 25). In one aspect, the recurrent plant has a T position 101 in SEQ ID NO 25 (or in a sequence comprising substantial sequence identity to SEQ ID NO: 25).

In one embodiment of the invention, SNP_07 is characterized in that the ToLCNDV resistant donor plant has a C at position 101 in SEQ ID NO 25 (or in a sequence comprising substantial sequence identity to SEQ ID NO: 25) and the recurrent plant has a T at position 101 in SEQ ID NO 25 (or in a sequence comprising substantial sequence identity to SEQ ID NO: 25).

As SEQ ID NO: 25 corresponds to the (−) strand of the double stranded DNA of each chromosome 5, an alternative way of referring to SNP_07 is to refer to the SNP at position 101 of the complementary strand of SEQ ID NO: 25. The ToLCNDV resistant donor plant has a 'G' (Guanine) at position 101 of the complementary strand of SEQ ID NO: 25 or in a sequence comprising substantial sequence identity to the complementary strand of SEQ ID NO: 25.

In one embodiment of the invention, SNP_07 is characterized in that the donor plant has a G at position 101 of the complementary strand of SEQ ID NO 25 (or at the equivalent position of a sequence comprising substantial sequence identity to the complementary strand of SEQ ID NO: 25) and the recurrent plant has an A at position 101 of the complementary strand of SEQ ID NO 25.

"SNP_08" which is alternatively designated "mME72209" is to be understood in context with the present invention to be a SNP at position 101 in SEQ ID NO 26. SEQ ID NO 26 or a sequence substantially identical to SEQ ID NO 26 can be found on chromosome 5. The position of SNP_08 on the chromosome of the reference genome is given in Table 3. Preferably the nucleotide sequence comprising SNP_08 has a nucleotide sequence having at least 85% identity with the nucleotide sequence shown under SEQ ID NO 26, more preferably at least 90%, 91%, 92%, 93%, 94% identity with the nucleotide sequence shown under SEQ ID NO 26, further more preferably at least 95% identity with the nucleotide sequence shown under SEQ ID NO 26, even more preferred at least 97% identity with the nucleotide sequence shown under SEQ ID NO 26, even further more preferred at least 98% identity with the nucleotide sequence shown under SEQ ID NO 26, in particular preferred at least 99% identity with the nucleotide sequence shown under SEQ ID NO 26 or more particularly preferred at least 99.5% identity with the nucleotide sequence shown under SEQ ID NO 26 under the provision that in each case the nucleotide at position 101 in SEQ ID NO 26 is different from the corresponding nucleotide at the same position of the recurrent plant. Such sequences having at least 85%, 90%, 91%, 92%, 93%, 94%, 95%, 97%, 98%, 99% or more sequence identity to SEQ ID NO 26 are referred to as having substantial sequence identity to SEQ ID NO: 26.

The ToLCNDV resistant donor plants used in the invention have a 'G' (Guanine) at position 101 in SEQ ID NO 25 (or in a sequence comprising substantial sequence identity to SEQ ID NO: 25). In one embodiment of the invention, SNP_08 is characterized in that the recurrent plant has an A, T or C at position 101 in SEQ ID NO 26 (or in a sequence comprising substantial sequence identity to SEQ ID NO: 26). In one aspect, the recurrent plant has an A position 101 in SEQ ID NO 26 (or in a sequence comprising substantial sequence identity to SEQ ID NO: 26).

In one embodiment of the invention, SNP_08 is characterized in that the ToLCNDV resistant donor plant has a G at position 101 in SEQ ID NO 26 (or in a sequence comprising substantial sequence identity to SEQ ID NO: 26) and the recurrent plant has an A at position 101 in SEQ ID NO 26 (or in a sequence comprising substantial sequence identity to SEQ ID NO: 26).

As SEQ ID NO: 26 corresponds to the (−) strand of the double stranded DNA of each chromosome 5, an alternative way of referring to SNP_08 is to refer to the SNP at position 101 of the complementary strand of SEQ ID NO: 26. The ToLCNDV resistant donor plant has a 'C' (Cytosine) at position 101 of the complementary strand of SEQ ID NO: 26 or in a sequence comprising substantial sequence identity to the complementary strand of SEQ ID NO: 26.

In one embodiment of the invention, SNP_08 is characterized in that the donor plant has a C at position 101 of the complementary strand of SEQ ID NO 26 (or at the equivalent position of a sequence comprising substantial sequence identity to the complementary strand of SEQ ID NO: 26) and the recurrent plant has an T at position 101 of the complementary strand of SEQ ID NO 26.

TABLE 1

| Marker name | Marker type | Chrom | Pseudo-molecule coordinates | cM Garcia-Mas et al. (2012) | cM Argyris et al. (2015) | LG_ICuGI | cM_ICuGI | Scaffold v3.5.1 (world wide web at melonomics.net) | Scaffold coordinates |
|---|---|---|---|---|---|---|---|---|---|
| CMPSNP460 | SNP | 5 | 12.966.671 | 57.3 | | | | CM3.5.1_scaffold00009 | 1.816.109 |
| SNP_06 | SNP | 5 | | | | | | CM3.5.1_scaffold00009 | 2.607.437 |
| CMPSNP682 | SNP | 5 | 15.854.444 | 57.3 | 50.4 | | | CM3.5.1_scaffold00009 | 4.703.882 |
| CMN62_05 | SSR | 5 | 16.570.623 | | | | | CM3.5.1_scaffold00009 | 5.420.061 |
| CMPSNP1005 | SNP | 5 | 17.239.621 | 57.3 | 50.4 | | | CM3.5.1_scaffold00009 | 6.089.059 |
| CMN61_15 | SSR | 5 | 17.453.772 | | | | | CM3.5.1_scaffold00009 | 6.303.210 |
| CMPSNP39 | SNP | 5 | 17.651.074 | 57.3 | | | | CM3.5.1_scaffold00009 | 6.500.512 |
| PS_03-B08 | SNP | 5 | 18.119.560 | 57.3 | 50.4 | | | CM3.5.1_scaffold00009 | 6.968.998 |
| ECM203 | SSR | 5 | 18.459.732 | | | | | CM3.5.1_scaffold00009 | 7.309.170 |
| CMPSNP2005 | SNP | 5 | 18.833.037 | | 50.4 | | | CM3.5.1_scaffold00009 | 7.682.475 |
| CMN01_49 | SSR | 5 | 19.305.580 | | | | | CM3.5.1_scaffold00003 | 26.051 |
| ECM142 | SSR | 5 | 19.743.282 | | | 5 | 54 | CM3.5.1_scaffold00003 | 463.753 |
| CMGAN3 | SSR | 5 | 19.871.767 | | | 5 | 56 | CM3.5.1_scaffold00003 | 592.238 |
| CMPSNP1018 | SNP | 5 | 20.088.198 | 50.9 | 50.7 | | | CM3.5.1_scaffold00003 | 808.669 |
| CMPSNP613 | SNP | 5 | 20.406.864 | | | | | CM3.5.1_scaffold00003 | 1.127.335 |
| CMN05_89 | SSR | 5 | 21.514.552 | | | | | CM3.5.1_scaffold00003 | 2.235.023 |
| CMN23_06 | SSR | 5 | 21.949.502 | | | | | CM3.5.1_scaffold00003 | 2.669.973 |
| GCM295 | SSR | 5 | 23.318.454 | | | | | CM3.5.1_scaffold00003 | 4.038.925 |
| CMPSNP741 | SNP | 5 | 23.620.132 | | | | | CM3.5.1_scaffold00003 | 4.340.603 |
| ECM115 | SSR | 5 | 23.786.719 | | | | | CM3.5.1_scaffold00003 | 4.507.190 |
| CMPSNP1136 | SNP | 5 | 24.100.004 | 67.0 | 67.7 | | | CM3.5.1_scaffold00003 | 4.820.475 |
| ECM206 | SSR | 5 | 24.175.232 | | | | | CM3.5.1_scaffold00003 | 4.895.703 |
| CMCTN2 | SSR | 5 | 24.313.118 | | | 5 | 73 | CM3.5.1_scaffold00003 | 5.033.589 |
| CMGAAN144 | SSR | 5 | 24.403.405 | | | 5 | 73 | CM3.5.1_scaffold00003 | 5.123.876 |
| SNP_05 | SNP | 5 | | | | | | CM3.5.1_scaffold00003 | 5.202.092 |
| 3J84-496 | SNP | 5 | 24.884.331 | | | | | CM3.5.1_scaffold00003 | 5.604.802 |
| 3J84-19 | SNP | 5 | 24.884.834 | | | | | CM3.5.1_scaffold00003 | 5.605.305 |
| 60k53-404 | SNP | 5 | 25.036.462 | | | | | CM3.5.1_scaffold00003 | 5.756.933 |
| 60k53-147 | SNP | 5 | 25.036.692 | | | | | CM3.5.1_scaffold00003 | 5.757.163 |
| 60k53-80 | SNP | 5 | 25.036.780 | | | | | CM3.5.1_scaffold00003 | 5.757.251 |
| 60k49-351 | SNP | 5 | 25.040.592 | | | | | CM3.5.1_scaffold00003 | 5.761.063 |
| 60k49-307 | SNP | 5 | 25.040.689 | | | | | CM3.5.1_scaffold00003 | 5.761.160 |
| 60k49-182 | SNP | 5 | 25.040.770 | | | | | CM3.5.1_scaffold00003 | 5.761.241 |

TABLE 1-continued

| Marker name | Marker type | Chrom | Pseudo-molecule coordinates | cM Garcia-Mas et al. (2012) | cM Argyris et al. (2015) | LG_ICuGI | cM_ICuGI | Scaffold v3.5.1 (world wide web at melonomics.net) | Scaffold coordinates |
|---|---|---|---|---|---|---|---|---|---|
| 60k45.389 | SNP | 5 | 25.043.452 | 73.4 | | | | CM3.5.1_scaffold00003 | 5.763.923 |
| 60k45.288 | SNP | 5 | 25.043.521 | | | | | CM3.5.1_scaffold00003 | 5.763.992 |
| 60k45.213 | SNP | 5 | 25.043.624 | | | | | CM3.5.1_scaffold00003 | 5.764.095 |
| 60k45.14 | SNP | 5 | 25.043.807 | 73.4 | | | | CM3.5.1_scaffold00003 | 5.764.278 |
| 60k42-490 | SNP | 5 | 25.045.798 | | | | | CM3.5.1_scaffold00003 | 5.766.269 |
| 60k42-411 | SNP | 5 | 25.045.907 | | | | | CM3.5.1_scaffold00003 | 5.766.378 |
| 60k42-126 | SNP | 5 | 25.046.183 | 76.6 | | | | CM3.5.1_scaffold00003 | 5.766.654 |
| 60k42-29 | SNP | 5 | 25.046.269 | | | | | CM3.5.1_scaffold00003 | 5.766.740 |
| 60k41.333 | SNP | 5 | 25.047.374 | | | | | CM3.5.1_scaffold00003 | 5.767.845 |
| 60k41.243 | SNP | 5 | 25.047.449 | 73.4 | | | | CM3.5.1_scaffold00003 | 5.767.920 |
| 60k41.49 | SNP | 5 | 25.047.654 | | | | | CM3.5.1_scaffold00003 | 5.768.125 |
| SNP_04 | SNP | 5 | | | | | | CM3.5.1_scaffold00003 | 5.785.550 |
| CMTAAN128 | SSR | 5 | 25.081.134 | | | 5 | 72 | CM3.5.1_scaffold00003 | 5.801.605 |
| CMTAN138 | SSR | 5 | 25.081.134 | | | 5 | 70 | CM3.5.1_scaffold00003 | 5.801.605 |
| CMTAN139 | SSR | 5 | 25.081.134 | | | 5 | 70 | CM3.5.1_scaffold00003 | 5.801.605 |
| CMPSNP588 | SNP | 5 | 25.271.831 | 75.0 | 78.3 | | | CM3.5.1_scaffold00003 | 5.992.302 |
| CMPSNP464 | SNP | 5 | 25.639.164 | 75.8 | | | | CM3.5.1_scaffold00003 | 6.359.635 |
| SNP_03 | SNP | 5 | | | | | | CM3.5.1_scaffold00003 | 6.553.350 |
| CMPSNP 1155 | SNP | 5 | 26.124.693 | 79.8 | | | | CM3.5.1_scaffold00003 | 6.845.164 |
| SNP_02 | SNP | 5 | | | | | | CM3.5.1_scaffold00003 | 6.950.286 |
| CMPSNP690 | SNP | 5 | 26.340.629 | 79.8 | 90.0 | | | CM3.5.1_scaffold00003 | 7.061.100 |
| CMTCN227 | SSR | 5 | 26.453.003 | | | 5 | 61 | CM3.5.1_scaffold00003 | 7.173.474 |
| CMPSNP1115 | SNP | 5 | 26.639.938 | 84.6 | | | | CM3.5.1_scaffold00003 | 7.360.409 |
| ECM213 | SSR | 5 | 26.907.003 | | | | | CM3.5.1_scaffold00003 | 7.627.474 |
| SNP_01 | SNP | 5 | | | | | | CM3.5.1_scaffold00003 | 7.824.960 |
| AI_13-H12 | SNP | 5 | 27.276.249 | 89.4 | | | | CM3.5.1_scaffold00003 | 7.996.720 |

The molecular markers described herein may be detected according to standard methods. For example SNP markers can be detected using a KASP-assay (see \Vww.kpbioscience.co.uk) or other assays. A KASP-assay has been developed for SNPs described herein. Respective details are disclosed in the Example section. Sequences used in the respective KASP-assays are given in the Sequence Listing. For developing KASP-assays for the SNPs two allele specific forward primers and one allele specific reverse primer were designed according to common general knowledge (see e.g. Allen et al. 2011, Plant Biotechnology J. 9, 1 0 86-1 099, especially p097-098 for KASP assay method).

"Sequence identity" and "sequence similarity" can be determined by alignment of two peptide or two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) share at least a certain minimal percentage of sequence identity defined further below). These programs use the Needleman and Wunsch global alignment algorithm to align two sequences over their entire length, maximizing the number of matches and minimizes the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1 992, PNAS 89, 1 09 1 5-1 09 1 9). Sequence alignments and scores for percentage sequence identity may for example be determined using computer programs, such as EMBOSS as available on the world wide web under ebi.ac.uk/Tools/psa/emboss needle/). Alternatively sequence similarity or identity may be determined by searching against databases such as FASTA, BLAST, etc., but hits should be retrieved and aligned pairwise to compare sequence identity. Two proteins or two protein domains, or two nucleic acid sequences have "substantial sequence identity" if the percentage sequence identity is at least 85%, 90%, 95%, 98%, 99% or more (e.g. at least 99.1, 99.2, 99.3, 99.4, 99.5, 99.6, 99.7, 99.8, 99.9 or more (as determined by Emboss "needle" using default parameters, i.e. gap creation penalty=10, gap extension penalty=0.5, using scoring matrix DNAFULL for nucleic acids an Blosum62 for proteins).

When reference is made to a nucleic acid sequence (e.g. DNA or genomic DNA) having "substantial sequence identity to" a reference sequence or having a sequence identity of at least 80%, e.g. at least 85%, 90%, 95%, 98%, 99%, 99.2%, 99.5%, 99.9% nucleic acid sequence identity to a reference sequence, in one embodiment said nucleotide sequence is considered substantially identical to the given nucleotide sequence and can be identified using stringent hybridization conditions. In another embodiment, the nucleic acid sequence comprises one or more mutations compared to the given nucleotide sequence but still can be identified using stringent hybridisation conditions.

Cultivated melon plants comprising a ToLCNDV resistance conferring fragment introgressed on chromosome 5 show reduced symptoms when infected with ToLCNDV, while susceptible controls (lacking the introgression fragment) show the expected severe symptoms in the same conditions.

In a preferred embodiment of the invention, plant cells according to the invention or plants according to the invention are characterized in that they upon infection with ToLCNDV show an average symptom level of at least 4.0, more preferably at least 5.0. As mentioned previously, QTL5 confers resistance when the QTL is in homozygous or heterozygous form. A ToLCNDV susceptible plant into which the introgression fragment comprising QTL5 is introduced by e.g. backcrossing and which is optionally selfed to generate a homozygous introgression fragment (comprising the donor genotype for one or more or all of SNP_01, SNP_02, SNP_03, SNP_07, SNP_08, SNP_04, SNP_05 and SNP_06 in homozygous form), will result in a plant which is resistant to ToLCNDV infection, having an average disease score of at least 4.0, preferably at least 5.0, preferably at least 6.0 or preferably at least 7.0. Symptom levels occurring after infection with ToLCNDV between 1 and 9, wherein 1 is defined to be the level with the most severe symptoms and 9 is defined as the highest resistance level, have been described herein above and are applicable here accordingly. A preferred test for determining the symptom levels is given below under "General Methods".

In another embodiment of the invention, plant cells according to the invention or plants according to the invention are characterized in that they upon infection with ToLCNDV show a symptom level between 4 and 6, more preferably a symptom level of between 5 and 6, while the susceptible controls show a symptom level of 2 or less.

Resistance to ToLCNDV conferred by the introgression fragment is expressed in a dominant manner and thus can be observed when only one chromosome 5 comprises the introgression fragment comprising the sequence of the donor plant between the markers of chromosome 5 disclosed herein.

Other specific embodiments of the present invention therefore relate to melon plant cells according to the invention, or melon plants according to the invention, wherein the introgression fragment from chromosome 5 of a ToLCNDV resistant donor plant comprising the sequence of the donor plant in-between SNP_01 and SNP_06, in-between SNP_01 and SNP_05, in-between SNP_01 and SNP_04, in-between SNP_02 and SNP_06, in-between SNP_02 and SNP_05, in-between SNP_02 and SNP_04, in-between SNP_03 and SNP_06, in-between SNP_03 and SNP_05 or preferably in-between SNP_03 and SNP_04, or between SNP_07 and SNP_08, or between SNP_03 and SNP_08, or between SNP_08 and SNP_04, is present in heterozygous state. Accordingly, it is sufficient that at least one chromosome 5 in the plant cells according to the invention or plants according to the invention comprise the just described introgression fragment. It is however understood, that chromosome 5 in respect to the just described introgression fragment can also be present in the homozygous state without diminishing the degree of resistance, because of the dominance of the ToLCNDV resistance conferred by the just described introgression fragment. Thus, the invention comprises plant cells according to the invention or plants according to the invention which comprise the just described introgression fragment in a heterozygous or homozygous state.

Table 2 illustrates the SNP genotype of plants or cells comprising the ToLCNDV resistant donor SNPs in homozygous form or heterozygous form, as well as the recurrent parent SNP genotype, lacking the introgression fragment.

| SNP and nucleotide position (nt) in the sequence | SNP genotype in melon plant comprising the donor fragment in homozygous form | SNP genotype in melon plant comprising the donor fragment in heterozygous form | SNP genotype of the recurrent parent, lacking the introgression fragment |
|---|---|---|---|
| SNP_01 (nt 101 of SEQ ID NO 1*) | CC | CT | TT |
| SNP_02 (nt 945 of SEQ ID NO 2*) | TT | TG | GG |
| SNP_03 (nt 68 of SEQ ID NO 3*) | TT | TC | CC |
| SNP_07 (nt 101 of SEQ ID NO: 25*) | CC | CT | TT |
| SNP_08 (nt 101 of SEQ ID NO: 26*) | GG | GA | AA |
| SNP_04 (nt 227 of SEQ ID NO 4*) | AA | AG | GG |
| SNP_05 (nt 839 of SEQ ID NO 5*) | CC | CT | TT |
| SNP_06 (nt 445 of SEQ ID NO 6*) | AA | AG | GG |

*or the nucleotide (nt) at the equivalent position in a sequence comprising at least 90%, 91%, 92%, 93%, 94%, 95%, 96%, 97%, 98% sequence identity to the given sequence.

In one embodiment, a cultivated melon plant (of the species C. melo) is provided which comprises a recombinant chromosome 5, whereby the recombinant chromosome 5 comprises an introgression fragment that confers ToLCNDV resistance onto the melon plant when present in homozygous or heterozygous form and wherein the introgression fragment is from a wild donor of the species C. melo. In one aspect the introgression fragment comprises the SNP donor genotype for one or more or all of SNP_01, SNP_02, SNP_03, SNP_07, SNP_08, SNP_04, SNP_05 and/or SNP_06. In one embodiment the introgression fragment comprises the donor SNP genotype for at least SNP_03 and/or SNP_04, or for at least SNP_07 and/or SNP_08. The SNP genotype of the donor may be present in homozygous form (if the introgression fragment is in homozygous form) or in heterozygous form (if the introgression fragment is in heterozygous form). So, for example, the plant or plant cell or plant part may comprise the TT or TC genotype for SNP_03 at nucleotide 68 of SEQ ID NO: 3. Thus, the plant, plant cell, or plant part may comprise SEQ ID NO: 3, or a sequence comprising at least 95%, 97%, or 98% sequence identity to SEQ ID NO: 3, in homozygous form or in heterozygous form.

In one embodiment, cultivated melon plants or cells of these plants are provided which comprise an introgression fragment from a wild donor on chromosome 5, which introgression fragment confers the ToLCNDV resistance, whereby the introgression fragment lies in-between SNP_01 and SNP_06 (or in-between SEQ ID NO:1 and SEQ ID NO:6, or a sequence comprising at least 90%, or at least 95%, or at least 97% or 98% sequence identity to SEQ ID NO: 1 or to SEQ ID NO 6); or whereby the introgression fragment lies in-between SNP_01 and SNP_05 (or in-between SEQ ID NO:1 and SEQ ID NO:5, or a sequence comprising at least 90%, or at least 95%, or at least 97% or 98% sequence identity to SEQ ID NO: 1 or to SEQ ID NO 5), or whereby the introgression fragment lies in-between SNP_03 and SNP_04 (or in-between SEQ ID NO: 3 and SEQ ID NO: 4, or a sequence comprising at least 90%, or at least 91%, or at least 92% 93%, 94%, or at least 95%, or at least 97% or 98% sequence identity to SEQ ID NO: 3 or to SEQ ID NO: 4).

In one aspect, the cultivated melon plants or cells of these plants comprise an introgression fragment from a wild donor on chromosome 5, which introgression fragment confers the ToLCNDV resistance, whereby the introgression fragment lies in-between SNP_01 and SNP_06 (or in-between SEQ ID NO: 1 and SEQ ID NO: 6, or a sequence comprising at least 90%, or at least 95%, or at least 97% or 98% sequence identity to SEQ ID NO: 1 or to SEQ ID NO 6), or the fragment lies in-between SNP_01 and SNP_05 (or in-between SEQ ID NO:1 and SEQ ID NO:5, or a sequence comprising at least 90%, or at least 95%, or at least 97% or 98% sequence identity to SEQ ID NO: 1 or to SEQ ID NO 5), or whereby the introgression fragment lies in-between SNP_03 and SNP_04 (or in-between SEQ ID NO: 3 and SEQ ID NO: 4, or a sequence comprising at least 90%, or at least 91%, or at least 92% 93%, 94%, or at least 95%, or at least 97% or 98% sequence identity to SEQ ID NO: 3 or to SEQ ID NO: 4) and whereby the introgression fragment comprises a Cytosine (C) at nucleotide 101 of SEQ ID NO: 25 or at the equivalent nucleotide of a sequence comprising substantial sequence identity to SEQ ID NO: 25 and/or whereby the introgression fragment comprises a Guanine (G) at nucleotide 101 of SEQ ID NO: 26 or at the equivalent nucleotide of a sequence comprising substantial sequence identity to SEQ ID NO: 26; and optionally whereby the introgression fragment comprises a Thymine (T) at nucleotide 68 of SEQ ID NO: 3 or at the equivalent nucleotide of a sequence comprising substantial sequence identity to SEQ ID NO: 3 and/or an Adenine (A) at nucleotide 227 of SEQ ID NO: 4 or at the equivalent nucleotide of a sequence comprising substantial sequence identity to SEQ ID NO: 4.

In a further aspect, the introgression fragment comprises a Thymine (T) at nucleotide 68 of SEQ ID NO: 3 or at the equivalent nucleotide of a sequence comprising substantial sequence identity to SEQ ID NO: 3 and/or a Cytosine (C) at nucleotide 101 of SEQ ID NO: 25 or at the equivalent nucleotide of a sequence comprising substantial sequence identity to SEQ ID NO: 25 and/or a Guanine (G) at nucleotide 101 of SEQ ID NO: 26 or at the equivalent nucleotide of a sequence comprising substantial sequence identity to SEQ ID NO: 26 and/or an Adenine (A) at nucleotide 227 of SEQ ID NO: 4 or at the equivalent nucleotide of a sequence comprising substantial sequence identity to SEQ ID NO: 4.

In a further aspect, the introgression fragment comprises a Thymine (T) at nucleotide 68 of SEQ ID NO: 3 or at the equivalent nucleotide of a sequence comprising substantial sequence identity to SEQ ID NO: 3 and/or a Guanine (G) at nucleotide 101 of the complementary strand of SEQ ID NO: 25 or at the equivalent nucleotide of a sequence comprising substantial sequence identity to the complementary strand of SEQ ID NO: 25 and/or a Cytosine (C) at nucleotide 101 of the complementary strand of SEQ ID NO: 26 or at the equivalent nucleotide of a sequence comprising substantial sequence identity to the complementary strand of SEQ ID NO: 26 and/or an Adenine (A) at nucleotide 227 of SEQ ID NO: 4 or at the equivalent nucleotide of a sequence comprising substantial sequence identity to SEQ ID NO: 4.

In a further aspect, the introgression fragment comprises the donor nucleotide of SNP_03, SNP_07 and SNP_08 or the donor nucleotide of SNP_07, SNP_08 and SNP_04.

In a further aspect, the introgression fragment optionally further comprises the donor nucleotide of SNP_02 and/or SNP_05. Thus, the introgression fragment may comprise the donor genotype for SNP_02, SNP_03, SNP_07, SNP_08; or for SNP_07, SNP_08, SNP_04 and SNP_05, or for SNP_02, SNP_03, SNP_07, SNP_08, and SNP_04; or for SNP_02, SNP_03, SNP_07, SNP_08, SNP_04 and SNP_05.

In another aspect, the introgression fragment optionally further comprises the donor nucleotide of SNP_02 and/or SNP_01. Thus, the introgression fragment may comprise the donor genotype for SNP_02, SNP_03, SNP_07 and optionally SNP_08; or for SNP_01, SNP_02 and SNP_03, SNP_07 and optionally SNP_08; and optionally also for SNP_04, and further optionally also for SNP_05, and further optionally for SNP_06.

In yet another aspect, the introgression fragment optionally further comprises the donor nucleotide of SNP_08, SNP_04, SNP_05 and/or SNP_06.

Thus in one aspect, the cultivated melon plants or cells of these plants comprise an introgression fragment from a wild donor on chromosome 5, which introgression fragment confers the ToLCNDV resistance, whereby the introgression fragment lies in-between SNP_01 and SNP_06 (or in-between SEQ ID NO:1 and SEQ ID NO:6, or a sequence comprising at least 90%, or at least 95%, or at least 97% or 98% sequence identity to SEQ ID NO: 1 or to SEQ ID NO 6) and whereby the introgression fragment comprises the ToLCNDV resistant SNP genotype for one or more or all of SNP_01, SNP_02, SNP_03, SNP_07, SNP_08, SNP_04, SNP_05, and SNP_06. In one aspect, the fragment comprises the donor SNP genotype for SNP_07 and/or SNP_08, optionally also for SNP_03 and/or SNP_04.

Thus, in one aspect, the cultivated melon plants or cells of these plants comprise an introgression fragment from a wild donor on chromosome 5, which introgression fragment confers the ToLCNDV resistance, whereby the introgression fragment lies in-between SNP_01 and SNP_05 (or in-between SEQ ID NO:1 and SEQ ID NO:5, or a sequence comprising at least 90%, or at least 95%, or at least 97% or 98% sequence identity to SEQ ID NO: 1 or to SEQ ID NO 5) and whereby the introgression fragment comprises the ToLCNDV resistant SNP genotype for one or more or all of SNP_01, SNP_02, SNP_03, SNP_07, SNP_08, SNP_04 and SNP_05. In one aspect, the fragment comprises the donor SNP genotype for SNP_07 and/or SNP_08, optionally also for SNP_03 and/or SNP_04. Optionally the resistant SNP genotype is also present for SNP_06.

Thus, in another aspect, the cultivated melon plants or cells of these plants comprise an introgression fragment from a wild donor on chromosome 5, which introgression fragment confers the ToLCNDV resistance, whereby the introgression fragment lies in-between SNP_03 and SNP_04 (or in-between SEQ ID NO:3 and SEQ ID NO:4, or a sequence comprising at least 90%, or at least 95%, or at least 97% or 98% sequence identity to SEQ ID NO: 3 or to SEQ ID NO 4) and whereby the introgression fragment comprises the ToLCNDV resistant SNP genotype for SNP_07 and/or SNP_08, and optionally further comprises the ToLCNDV resistant SNP genotype for SNP_03 and/or SNP_04. Optionally the donor genotype is also present for one or more or all of SNP markers selected from SNP_01, SNP_02, SNP_05 and SNP_06.

In a further aspect, the cultivated melon plants or cells of these plants comprise an introgression fragment from a wild donor on chromosome 5, which introgression fragment confers the ToLCNDV resistance, whereby the introgression fragment lies in-between SNP_02 and SNP_04 (or in-between SEQ ID NO:2 and SEQ ID NO:4, or a sequence comprising at least 90%, or at least 95%, or at least 97% or 98% sequence identity to SEQ ID NO: 2 or to SEQ ID NO 4) and whereby the introgression fragment comprises the ToLCNDV resistant SNP genotype for SNP_07 and/or SNP_08, and optionally further comprises the ToLCNDV resistant SNP genotype for SNP_02 and/or SNP_03 and/or SNP_04. Optionally the donor genotype is also present for one or more or all of SNP markers selected from SNP_01, SNP_05 and SNP_06.

Plants comprising plant cells according to the invention are another embodiment of the invention.

The melon plant according to the invention may be an inbred line, an open pollinated variety (OP) or an F1 hybrid. In one aspect the F1 hybrid comprises the introgression fragment in heterozygous form, i.e. produced by crossing two inbred parent lines, one of which possesses the introgression fragment (preferably in homozygous form, although not necessarily) and collecting the F1 hybrid seeds from said cross. The F1 hybrid may also comprise the introgression fragment in homozygous form, i.e. produced by crossing two inbred parent lines, each comprising the introgression fragment in homozygous or heterozygous form.

The melon plant according to the invention may be of any type. Preferably it has good agronomic and good fruit quality characteristics, such as large average fruit size (at least 500 g, 600 g, 700 g, 800 g, 900 g, 1000 g or more), high average brix of the fruits (e.g. an average refractometer % total soluble solids of at least 10%, 12%, 14%, 16%, 18% or more), many fruits being produced per plant, firm fruit flesh, etc.

Also other resistances may be introduced into the melon plants of the invention, such as resistance to one or more of the following diseases: Bacterial Wilt, Root Rot, Crown Blight, Melon Rust, Powdery Mildew, Verticillum Wilt, Sulphur Bum, Scab, Watermelon Mosaic, Downy Mildew, *Fusarium oxysporum* fsp. *melonis* (Fom) race 0, *Fusarium oxysporum* fsp. *melonis* (Fom) race 1, *Fusarium oxysporum* fsp. *melonis* (Fom) race 2, *Fusarium oxysporum* fsp. *melonis* (Fom) race 1.2, *Fusarium* Wilt R2, Root Knot (Nematode), Anthracnose, Cucumber Mosiac, and Squash Mosaic, and/or resistance to one or more of the following pests: Aphid resistance, Pickle Worm, Darkling Ground Beetle, Banded Cucumber Beetle, Mite, Western Spotted Cucumber Beetle, Melon Leafhopper, Melon Worm, Western Striped Cucumber Beetle or Melon Leafminer. Other resistance genes, against pathogenic viruses, fungi, bacteria or pests may also be introduced.

A specific aspect of the invention concerns plants or plant cells comprising an introgression fragment according to the invention which introgression fragment is obtainable from seeds deposited under NCIMB 42585 or from progeny thereof. The seeds deposited are cultivated melon plants of the BC4S4 generation comprising the introgression fragment in homozygous form, with the donor nucleotide being present in homozygous form for SNP_01, SNP_02, SNP_03, SNP_07, SNP_08, SNP_04, SNP_05 and SNP_06. The ToLCNDV resistance is located in-between SNP_03 and SNP_04, linked to the markers SNP_07 and/or SNP_08, which means that the size of the donor introgression can be reduced, by selecting recombinants having smaller introgression fragment sizes. So plants comprising sub-fragments of the introgression fragment (wherein said sub-fragments still confer ToLCNDV resistance), comprising the donor SNP for SNP_07 and/or SNP_08 and optionally also for SNP_03 and/or SNP_04, but having the SNP genotype of the recurrent parent for one or more or all of the other SNPs can be generated in ways known to the skilled person. In one aspect, SNP_08 was found to be linked most closely to the resistance and SNP_07 was found closely linked and unique in a large collection of melons tested. The resistance could lie between SNP_08 and SNP_07 or between SNP_08 and SNP_04 or in between SNP_03 and SNP_08. Further finemapping could be done to narrow down the region even further.

Whether a plant comprises the ToLCNDV resistance from the deposited seeds (either an introgression fragment of the same size or a sub-fragment thereof) can be determined by various methods, such as sequencing and comparing the sequences of the introgression fragments and recombination sites.

Melon plants and plant parts (such as leaves, stems, roots, fruits, pollen, flowers, etc.) comprising melon plant cells according to the invention are also an embodiment of the invention. Likewise seeds from which such plants can be grown are encompassed herein, as well as parts of such seeds (e.g. cells or tissues of the seeds such as the seed coat, embryo, etc.).

A further aspect of the present invention concerns melon seeds comprising an introgression fragment from chromosome 5 of a ToLCNDV resistant donor plant, wherein the introgression fragment comprises the sequence of the ToLCNDV resistant donor melon plant in-between SNP_01 and SNP_06, in-between SNP_01 and SNP_05, in-between SNP_01 and SNP_04, in-between SNP_02 and SNP_06, in-between SNP_02 and SNP_05, in-between SNP_02 and SNP_04, SNP_03 and SNP_06, in-between SNP_03 and SNP_05 or in-between SNP_03 and SNP_04, or in between SNP_07 and SNP_08, or in between SNP_08 and SNP_04, or in between SNP_03 and SNP_08. In a preferred embodiment of the invention the seeds comprise an introgression fragment from chromosome 5 of a ToLCNDV resistant donor plant, wherein the introgression fragment comprises the sequence of the ToLCNDV resistant donor melon plant in-between SNP_01 and SNP_06, more preferably in-between SNP_01 and SNP_05, even more preferably in-between SNP_02 and SNP_05, furthermore preferably in-between SNP_02 and SNP_04 and most preferably in-between SNP_03 and SNP_04.

Another embodiment of the invention concerns melon seeds obtainable or obtained from plants according to the invention, or seeds comprising plant cells according to the invention.

A further aspect of the present invention concerns melon plant fruits comprising an introgression fragment from chromosome 5 of a ToLCNDV resistant donor plant, wherein the introgression fragment comprises the sequence of the ToLCNDV resistant donor melon plant in-between SNP_01 and SNP_06, in-between SNP_01 and SNP_05, in-between SNP_01 and SNP_04, in-between SNP_02 and SNP_06, in-between SNP_02 and SNP_05, in-between SNP_02 and SNP_04, SNP_03 and SNP_06, in-between SNP_03 and SNP_05 or in-between SNP_03 and SNP_04, or in between SNP_07 and SNP_08, or in between SNP_08 and SNP_04 or in between SNP_03 and SNP_08. In a preferred embodiment of the invention, the seeds comprise an introgression fragment from chromosome 5 of a ToLCNDV resistant donor plant, wherein the introgression fragment comprises the sequence of the ToLCNDV resistant donor melon plant in-between SNP_01 and SNP_06, more preferably in-between SNP_01 and SNP_05, even more preferably in-between SNP_02 and SNP_05, furthermore preferably in-between SNP_02 and SNP_04 and most preferably in-between SNP_03 and SNP_04.

Another embodiment of the invention concerns melon fruits obtainable or obtained from plants according to the invention, or fruits comprising plant cells according to the invention.

Preferably melon fruits according to the invention are characterized in that they comprise an introgression fragment from chromosome 5 of a ToLCNDV resistant donor plant comprising the sequence of the donor plant in-between SNP_01 and SNP_06, in-between SNP_01 and SNP_05, in-between SNP_01 and SNP_04, in-between SNP_02 and SNP_06, in-between SNP_02 and SNP_05, in-between SNP_02 and SNP_04, in-between SNP_03 and SNP_06, in-between SNP_03 and SNP_05 or preferably in-between SNP_03 and SNP_04, or in between SNP_07 and SNP_08, or in between SNP_08 and SNP_04 or in between SNP_03 and SNP_08 in heterozygous or homozygous state.

The preferred and further embodiments described herein for melon plant cells or melon plants according to the invention are applicable to also represent preferred and further embodiments of the melon fruits of melon plants according to the invention, accordingly.

A further aspect of the present invention concerns melon plant propagation material comprising an introgression fragment from chromosome 5 of a ToLCNDV resistant donor plant, wherein the introgression fragment comprises the sequence of the ToLCNDV resistant donor melon plant in-between SNP_01 and SNP_06, in-between SNP_01 and SNP_05, in-between SNP_01 and SNP_04, in-between SNP_02 and SNP_06, in-between SNP_02 and SNP_05, in-between SNP_02 and SNP_04, SNP_03 and SNP_06, in-between SNP_03 and SNP_05 or in-between SNP_03 and SNP_04, or in between SNP_07 and SNP_08, or in between SNP_08 and SNP_04 or in between SNP_03 and SNP_08. In a preferred embodiment of the invention the propagation material comprises an introgression fragment from chromosome 5 of a ToLCNDV resistant donor plant, wherein the introgression fragment comprises the sequence of the ToLCNDV resistant donor melon plant in-between SNP_01 and SNP_06, more preferably in-between SNP_01 and SNP_05, even more preferably in-between SNP_02 and SNP_05, furthermore preferably in-between SNP_02 and SNP_04 and most preferably in-between SNP_03 and SNP_04, or in between SNP_07 and SNP_08, or in between SNP_08 and SNP_04 or in between SNP_03 and SNP_08.

Another embodiment of the invention concerns melon plant propagation material obtainable or obtained from plants according to the invention, or melon plant propagation material comprising plant cells according to the invention.

The preferred and further embodiments described herein for plant cells or plants according to the invention are applicable to also represent preferred and further embodiments of the propagation material of melon plants according to the invention, accordingly.

The term "propagation material" comprises those components of the plant which are suitable for generating progeny via the vegetative (agamic) or generative (gamic, sexual) route. Suitable for vegetative propagation are, for example, cuttings, in vitro tissue, cell, protoplast, embryo or callus cultures, micropropagation methods, rhizomes or tubers. Other propagation material includes, for example, fruits, seeds, seedling, being homozygous or heterozygous for an chromosome 5 introgression fragment conferring ToLCNDV resistance etc. The propagation material in one aspect takes the form of cuttings which are propagated by grafting to another rootstock or in vitro tissue culture material, in particular embryo cultures. In particular preferred is propagation material in the form of in vitro tissue culture material, particularly in vitro embryo cultures.

In one aspect non-propagating plant cells comprising the recombinant chromosome 5 described herein are provided. In one aspect such non-propagating plant cells may however be part of a melon plant or melon plant part.

A further embodiment of the invention concerns a method for producing a ToLCNDV resistant melon plant comprising the following steps
a) selecting a ToLCNDV resistant donor plant
b) crossing the donor plant selected in step a) with a recurrent plant sensitive to ToLCNDV
c) obtaining seeds from the plants crossed in step b) and optionally
d) verifying if the plants grown from the seeds obtained in step c) are resistant to ToLCNDV and/or comprise one or more of the SNPs from the donor plant selected from the group of SNP_01, SNP_02, SNP_03, SNP_07, SNP_08, SNP_04, SNP_05 and SNP_06.

A ToLCNDV resistant donor plant in step a) in the method for producing a ToLCNDV resistant melon plant according to the invention can be selected by infection of melon plants with ToLCNDV and determining the level of symptoms of ToLCNDV infected melon plants as described elsewhere herein. The same is applicable for verification in steps b) and c) of the method for producing a ToLCNDV resistant melon plant according to the invention, if a plant is ToLCNDV sensitive or resistant, respectively.

In a preferred embodiment of the method for producing a ToLCNDV resistant melon plant according to the invention the ToLCNDV resistant donor plant in step a) comprises a fragment on chromosome 5 conferring ToLCNDV resistance, the fragment comprising the sequence of the donor plant in-between SNP_01 and SNP_06, in-between SNP_01 and SNP_05, in-between SNP_01 and SNP_04, in-between SNP_02 and SNP_06, in-between SNP_02 and SNP_05, in-between SNP_02 and SNP_04, in-between SNP_03 and SNP_06, in-between SNP_03 and SNP_05 or in-between SNP_03 and SNP_04, or in between SNP_07 and SNP_08, or in between SNP_08 and SNP_04 or in between SNP_03 and SNP_08 Most preferably the fragment on chromosome 5 conferring ToLCNDV resistance comprises the sequence in-between SNP_03 and SNP_04. In a specifically preferred embodiment of the invention, the method for producing a ToLCNDV resistant melon plant according to the invention the ToLCNDV resistant donor plant in step a) comprises the fragment of chromosome 5 conferring ToLCNDV resistance comprising the sequence in-between SNP_01 and SNP_06, in-between SNP_01 and SNP_05, in-between SNP_01 and SNP_04, in-between SNP_02 and SNP_06, in-between SNP_02 and SNP_05, in-between SNP_02 and SNP_04, in-between SNP_03 and SNP_06, in-between SNP_03 and SNP_05 or preferably in-between SNP_03 and SNP_04, or in between SNP_07 and SNP_08, or in between SNP_08 and SNP_04 or in between SNP_03 and SNP_08, as found in the seeds deposited under NCIMB 42585.

In a preferred embodiment of the invention the method for producing a ToLCNDV resistant melon plant according to the invention is used for producing a plant according to the invention. The preferred and further embodiments as described herein for the plants according to the invention are applicable accordingly to the method for producing a ToLCNDV resistant melon plant according to the invention.

Plants obtainable or obtained by a method for producing a ToLCNDV resistant melon plant according to the invention are also an embodiment of the invention.

A further embodiment of the invention concerns methods for producing melon seeds comprising the following steps
a) growing a melon plant comprising at least one chromosome 5 having an introgression fragment from chromosome 5 of a ToLCNDV resistant donor plant, the introgression fragment comprising the sequence of the donor plant in-between SNP_03 and SNP_04 and preferably comprising the resistant donor SNP nucleotide for SNP_07 and/or SNP_08,
b) harvesting the fruits of the melon plants grown in step a)
c) collecting the seeds from the fruits obtained in step b).
d) In a preferred embodiment of the invention the melon plants of steps a) of the method for producing melon seeds according to the invention has the specific characteristics described as preferred and further embodiments of the plants according to the invention. The preferred and further embodiments as described herein for the plants according to the invention are applicable accordingly to the method for producing a hybrid melon seed according to the invention.

Seeds obtainable the method for producing melon seeds according to the invention are also an embodiment of the invention.

Another embodiment of the invention concerns methods for producing hybrid melon seeds comprising the following steps
a) providing a first inbred melon plant comprising at least one chromosome 5 having an introgression fragment from chromosome 5 of a ToLCNDV resistant donor plant, the introgression fragment comprising the sequence of the donor plant in-between SNP_03 and SNP_04 and preferably comprising the resistant donor SNP nucleotide for SNP_07 and/or SNP_08,
b) providing a second inbred melon plant with or without a chromosome 5 having an introgression fragment from chromosome 5 of a ToLCNDV resistant donor plant, the introgression fragment comprising the sequence of the donor plant in-between SNP_03 and SNP_04 and preferably comprising the resistant donor SNP nucleotide for SNP_07 and/or SNP_08,
c) crossing the plant provided in step a) with the plant provided in step b)
d) selecting seeds obtained from the cross of step c).

"Inbred plant" or "inbred line" shall mean in connection with the present invention plants which have undergone several generations of selfing and are highly uniform in respect to their genetic setup and phenotypic appearance.

In a preferred embodiment of the invention the inbred lines of steps a) and b) of the method for producing hybrid melon seeds according to the invention has the specific characteristics described as preferred and further embodiments of the plants according to the invention. The preferred and further embodiments as described herein for the plants according to the invention are applicable accordingly to the method for producing a hybrid melon seed according to the invention.

Hybrid seeds obtainable or obtained by the method for producing hybrid melon seeds according to the invention are also an embodiment of the invention.

A further embodiment of the present invention are methods for producing a melon fruit comprising the following step
a) growing a plant comprising at least one chromosome 5 having an introgression fragment from chromosome 5 of a ToLCNDV resistant donor plant, the introgression fragment comprising the sequence of the donor plant in-between SNP_03 and SNP_04 and preferably comprising the resistant donor SNP nucleotide for SNP_07 and/or SNP_08,
b) harvesting the fruits produced by the plants grown in step a).

The term "fruit" in its botanical meaning is commonly understood to be a seed bearing structure developed from the ovary of angiosperm flowers.

Melon fruits obtainable or obtained by a method for producing a melon fruit according to the invention are also an embodiment of the invention.

Melon donor plants being resistant to ToLCNDV can be identified with the aid of the SNP markers, in particular one or more or all of SNP_01, SNP_02, SNP_03, SNP_07, SNP_08, SNP_04, SNP_05 and SNP_06 disclosed herein. The present invention therefore for the first time enables a person skilled in the art to identify donor plants from which an introgression fragment conferring ToLCNDV resistance to melon plants can be transferred into recurrent melon plants.

A further embodiment of the invention therefore pertains the use of one or more or all of SNP_01, SNP_02, SNP_03, SNP_07, SNP_08, SNP_04, SNP_05 or SNP_06 for identification of a ToLCNDV resistant melon plant or parts thereof (such as cells, fruits, leaves). Preferably the use pertains the identification of ToLCNDV resistant donor melon plants and/or recurrent melon plants, but also to the identification of breeding lines, cultivars or varieties containing a recombinant chromosome 5, e.g. the recombinant chromosome 5 derived from the seeds deposited herein, optionally comprising a subfragment of the introgression fragment present in the seeds deposited.

Another embodiment is the use of one or more or all of SNP_01, SNP_02, SNP_03, SNP_07, SNP_08, SNP_04, SNP_05 or SNP_06 for introgression of ToLCNDV resistance into a TolCNDV susceptible melon plant, especially a cultivated melon line or variety.

Also an embodiment of the invention is the use of one or more or all of SNP_01, SNP_02, SNP_03, SNP_07, SNP_08, SNP_04, SNP_05 or SNP_06 in breeding ToLCNDV resistant melon plants.

Also provided is a method of screening plants or plant material or DNA derived therefrom for the presence of a fragment on chromosome 5 conferring TolCNDV resistance. The method comprises the steps of:
a) screening the genomic DNA for the SNP genotype of one or more or all of SNP_01, SNP_02, SNP_03, SNP_07, SNP_08, SNP_04, SNP_05 and SNP_06;
b) and optionally selecting plants or plant material which comprise the resistant donor genotype of one or more or all of SNP_01, SNP_02, SNP_03, SNP_07, SNP_08, SNP_04, SNP_05 and SNP_06.

Also provided is a method for producing a cultivated *C. melo* plant comprising an introgression fragment on chromosome 5, wherein said introgression fragment comprises a ToLCNDV QTL, comprising:
a) crossing a first cultivated melon plant being susceptible to ToLCNDV with a second wild melon plant being resistant to ToLCNDV, wherein said second melon plant comprises the CC or CT genotype for SNP_01 in SEQ ID NO: 1, and/or the TT or TG genotype for SNP_02 in SEQ ID NO: 2, and/or the TT or TC genotype for the SNP_03 in SEQ ID NO: 3, and/or the CC or CT genotype for SNP_07 in SEQ ID NO: 25, and/or the GG or GA genotype for SNP_08 in SEQ ID NO: 26, and/or the AA or AG genotype for the SNP_04 in SEQ ID NO: 4, and/or the CC or CT genotype for SNP_05 in SEQ ID NO: 5, and/or the AA or AG genotype for SNP_06 in SEQ ID NO: 6;
b) collecting F1 seeds from said cross and backcrossing an F1 plant to the first melon plant to produce a backcross (BC1) population, or selfing said F1 plants one or more times to produce an F2 or F3 population, and optionally selfing the backcross population to produce a BC1S1 population, c) wherein said F2, F3, BC1 or BC1S1 plant comprises the CC or CT genotype for SNP_01 in SEQ ID NO: 1, and/or the TT or TG genotype for SNP_02 in SEQ ID NO: 2, and/or the TT or TC genotype for the SNP_03 in SEQ ID NO: 3, and/or the CC or CT genotype for SNP_07 in SEQ ID NO: 25, and/or the GG or GA genotype for SNP_08 in SEQ ID NO: 26, and/or the AA or AG genotype for the SNP_04 in SEQ ID NO: 4, and/or the CC or CT genotype for SNP_05 in SEQ ID NO: 5, and/or the AA or AG genotype for SNP_06 in SEQ ID NO: 6.

Also provided is a method for identifying or detecting a cultivated *C. melo* plant comprising an introgression fragment on chromosome 5, wherein said introgression fragment comprises a ToLCNDV-resistance allele, comprising:

a) screening a *Cucumis melo* plant using a molecular marker assay which detects at least one of SNP marker selected from the group consisting of: SNP_01 in SEQ ID NO: 1, SNP_02 in SEQ ID NO: 2, SNP_03 in SEQ ID NO: 3, SNP_07 in SEQ ID NO: 25, SNP_08 in SEQ ID NO: 26, SNP_04 in SEQ ID NO: 4, SNP_05 in SEQ ID NO: 5 and/or SNP_06 in SEQ ID NO: 6; and b) identifying and/or selecting a plant comprising the CC or CT genotype for SNP_01 in SEQ ID NO: 1, and/or the TT or TG genotype for SNP_02 in SEQ ID NO: 2, and/or the TT or TC genotype for the SNP_03 in SEQ ID NO: 3, and/or the CC or CT genotype for SNP_07 in SEQ ID NO: 25, and/or the GG or GA genotype for SNP_08 in SEQ ID NO: 26, and/or the AA or AG genotype for the SNP_04 in SEQ ID NO: 4, and/or the CC or CT genotype for SNP_05 in SEQ ID NO: 5, and/or the AA or AG genotype for SNP_06 in SEQ ID NO: 6.

A method of producing *C. melo* F1 hybrid plants comprising a ToLCNDV resistance phenotype is provided comprising:

a) crossing a first inbred melon plant comprising at least one recombinant chromosome 5, the recombinant chromosome 5 comprising an introgression fragment that confers ToLCNDV resistance onto the first inbred melon plant when present in homozygous or heterozygous form and wherein said introgression fragment is from a wild plant of the species *Cucumis melo*, with a second inbred melon plant with or without said at least one recombinant chromosome 5 and b) collecting F1 hybrid seeds from said cross.

Further encompassed is a method for producing a melon plant comprising ToLCNDV resistance on chromosome 5, said method comprising:

a) screening a wild melon accession or several wild melon accessions using a molecular marker assay which detects at least one of SNP marker selected from the group consisting of: SNP_01 in SEQ ID NO: 1, SNP_02 in SEQ ID NO: 2, SNP_03 in SEQ ID NO: 3, SNP_07 in SEQ ID NO: 25, SNP_08 in SEQ ID NO: 26, SNP_04 in SEQ ID NO: 4, SNP_05 in SEQ ID NO: 5 and/or SNP_06 in SEQ ID NO: 6 b) identifying and/or selecting a wild melon plant comprising the CC or CT genotype for SNP_01 in SEQ ID NO: 1, and/or the TT or TG genotype for SNP_02 in SEQ ID NO: 2, and/or the TT or TC genotype for the SNP_03 in SEQ ID NO: 3, and/or the CC or CT genotype for SNP_07 in SEQ ID NO: 25, and/or the GG or GA genotype for SNP_08 in SEQ ID NO: 26, and/or the AA or AG genotype for the SNP_04 in SEQ ID NO: 4, and/or the CC or CT genotype for SNP_05 in SEQ ID NO: 5, and/or the AA or AG genotype for SNP_06 in SEQ ID NO: 6.

c) optionally confirming ToLCNDV resistance in a resistance assay;

d) and optionally introgressing said ToLCNDV resistance from said wild accession into a cultivated melon plant.

A *Cucumis melo* plant, or part thereof, is provided comprising a recombinant chromosome 5, the recombinant chromosome 5 comprising an introgression fragment that confers ToLCNDV resistance onto the *Cucumis melo* plant when present in homozygous or heterozygous form and wherein said introgression fragment comprises one or more or all of the Single Nucleotide Polymorphism (SNP) markers of the group:

a) the CC or CT genotype for SNP_01 in SEQ ID NO: 1, the TT or TG genotype for SNP_02 in SEQ ID NO: 2, the TT or TC genotype for the SNP_03 in SEQ ID NO: 3, the CC or CT genotype for SNP_07 in SEQ ID NO: 25, the GG or GA genotype for SNP_08 in SEQ ID NO: 26, the AA or AG genotype for the SNP_04 in SEQ ID NO: 4, the CC or CT genotype for SNP_05 in SEQ ID NO: 5, and/or the AA or AG genotype for SNP_06 in SEQ ID NO: 6, b) and wherein said introgression fragment is from a wild plant of the species *Cucumis melo*, said wild plant having an average ToLCNDV disease score of at least 7.0 on a scale of 1=dead plant to 9=no symptoms.

c) In one aspect the cultivated melon plant comprises at least the CC or CT genotype for SNP_07 in SEQ ID NO: 25 and/or the GG or GA genotype for SNP_08 in SEQ ID NO: 26, d) In one aspect the cultivated melon plant further comprises at least the TT or TC genotype for the SNP_03 in SEQ ID NO: 3 and/or the AA or AG genotype for the SNP_04 in SEQ ID NO: 4.

In one aspect the ToLCNDV resistance QTL or the introgression fragment comprising the QTL is the obtainable from/can be obtained from/is as present in seeds of which a representative sample has been deposited under Accession Number NCIMB42585 or progeny thereof (whereby the progeny retain the ToLCNDV resistance).

Seed Deposit Information

A representative sample of seeds of a cultivated melon, designated *Cucumis melo* TOLCHR5, comprising an introgression fragment comprising TolCNDV resistance introgressed on chromosome 5 (backcross 4, selfing 4 generation, BC4S4), was deposited by Nunhems B.V. on 6 Jun. 2016 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit numbers NCIMB 42585.

The Applicant requests that samples of the biological material and any material derived therefrom be only released to a designated Expert in accordance with Rule 32(1) EPC or related legislation of countries or treaties having similar rules and regulation, until the mention of the grant of the patent, or for 20 years from the date of filing if the application is refused, withdrawn or deemed to be withdrawn.

Access to the deposit will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

Description of Sequences

Characters other than G (guanine), A (adenine), T (thymine) and C (cytosine) have the following meaning in the SEQ ID NOs shown in the sequence listing:

R: G or A
Y: T or C
M: A or C
K: G or T
S: G or C
W: A or T
H: A or C or T
B: G or T or C
V: G or C or A
D: G or A or T
N: G or A or T or C

In SEQ ID NO: 1 to SEQ ID NO: 8 the SNP nucleotide of the resistant donor is shown in bold and surrounded by lines. A SNP markers can be designed either to the forward strand (+ strand) of the double stranded DNA or to the reverse strand (− strand) of the DNA, which strands have been assigned as forward or reverse with respect to the reference genome sequence. For example, SEQ ID NO: 1 is, in the reference genome sequence of melon, the reverse strand, and the SNP_01 is 'C' on the reverse strand and is a G on the forward strand (the forward strand is the complementary strand of SEQ ID NO: 1).

```
SEQ ID NO: 1: Sequence of the ToLCNDV resistant donor plant comprising SNP_01.
(reverse strand in reference genome):
                                                                  SEQ ID NO: 1
agctggtgca aagctggcat tcaaatcgaa tgaagaaata gcagtacaag tgaagtcaat         60
tccactagat gaagtaatcc cggattcaga acgagtgctt |c|aataaaaa tcgatgttca      120 aggctgggaa tatcatgtgc taaaaggggc aaagagaatt ttgtcaagga agggcactga      180
agctccatat ctcatctatg                                                  200

SEQ ID NO 2: Sequence of the ToLCNDV resistant donor plant comprising SNP_02.
(forward strand in reference genome)
                                                                  SEQ ID NO: 2
ttgtaatcat ggccattgcc tgatytgcag aatgtggcgt cttgattggg cacggtctgg       60
atgaagttac tccaaagctt gtggaagtta atgggttctt ctcttcaccr tctgrtctcc      120
ttcccatcga caatgtggtt tcttcttcaa acacaaaaga aaccctgtt gaagctgtag       180 aagaaagctg tgagttcttt tctccactca gttctaggtt tagttttta tttgtttttt      240 ttttcttttt tccttttac ttgctttgag ctgtaggaca caacacaaaa tgataagaac      300
aaaaatcaat ctatgttatt gttgtcattg tctcgcctgc ctcttcaagg taactaggct      360
ataacactga tccaaaatgt ataatcttta ttgctaagta acttatattg caaagattgg      420
gatggaatag gagcataggt tgcatctaat agttttgtcc aactttggtt atagtttcag      480
ccagtttgtt cagatgaaat tcttagtgat tatcactaat ggaattgttt ttataaatgt      540
tgtaggtgtt gaaagaagtg aagaatatga aaaggaaagc aggggaaccg agaaggctga      600
aatcttaccg acaaaagcaa catctgaagc aggttctgaa gtccaacctg tttccagtga      660
ttctgctcag atggtaccca atatgttgga gctcggtgat gcttataagc tagctgtagg      720
tgctagagga ggaagacaat tgtctggcaa gcttttgaa caatggatyg ggaaggaatc      780
ttcaaaagtt agtgaagatc tgaagcttct cttgacacaa ctctcattta atcgtttgaa      840
tgaccaatca cgggagatga gtccaaggct gtccgtaaat ggagacgagg tgaggaactt      900
tgattacttg agygctgttg ggatgcaaat gctacaaaaa aggw|t|tcgc ttgaaagaaa      960 tgagtccggt gtagaatctt tagatggaag cataattagt gaaatcgatg gggaaaacat     1020
ggctgatagg ttgaaacgac agattgagta tgataagaag gttmtgartt ctttatacaa     1080
ggaattggag gaagaaagaa atgcatccgc aattgctgca aatcaggcaa tggccatgat     1140
tacaa                                                                1145
```

-continued

SEQ ID NO 3: Sequence of the ToLCNDV resistant donor plant comprising SNP_03.
(forward strand in reference genome)

```
                                                                    SEQ ID NO 3
agacggcgta catgcagcat tctgttaccc cgcgatgccc agcgatgaaa caactccttt          60 gcatcctEat ggtccagagg ttccagatca tacgactcac caaatgcagg aaacttaaat         120
ctagaggtga ccaaaatttt gcagttgggt aatcgggaga acttttca                     168
```

SEQ ID NO 4: Sequence of the ToLCNDV resistant donor plant comprising SNP_04.
(forward strand in reference genome)

```
                                                                    SEQ ID NO 4
ggagkcttca tccgtctttta ccttcctcac ttttttacct aaccaagtta cgtcttgtag         60
gttgcaagat aacaaatttg gatttcttag aaacaattgt ttatgttgcc ccttcrttga         120
aagagttgga cttgtccgaa aacaactttt gtagamtacc ctcrtgtatt attaatttta        180
aatccctgaa atatctttat acaatggatt gtgagttgct ygaagaaatt tcaaaggttc        240
cagaaggtgt aatttgtacg agtgccgcag gatgcaaatc attggctaga tttcccgaca        300
acttagctga tttcatatct tgtggtaatt ctgcggtgcg taccatatct ctttctcatg        360
acttcaccat tatctctagc tcatgtatat ttaatttcat tcatataata tatattactt        420
ataactattt actgatctca tggtgcagga atgttgtaaa ggtggatg                     468
```

SEQ ID NO 5: Sequence of the ToLCNDV resistant donor plant comprising SNP_05.
(reverse strand in reference genome)

```
                                                                   SEQ ID NO: 5
tgcaggtagt caaaccaatt gataatattt gctcaccatc aaaattggta accatagaca          60
tagaytgacc aagcccaggc aaaacggcat catcttfttg ttttctatca ttactattct        120
gattacccaa aagaaatctt cttttttgtac ttggagagaa ataatccccg tctgcacatt       180
gcatggaagg tgtgctgtca tgagcatcag cattacacac accagaatta gatttcttgc        240
tagccaagat ttcacaacca ccaagagaag caggacctac gcctggggtc tctgcctyag        300
aaagccaags atcaaagcac acttgtgaag gacctgaaac tgtctcagat ccagggattt       360
ctcctacatt gggtaagcta gcctgttcaa agccatcaca cacatctaca agcggcagtc        420
taccatacat ggaactatta gaataagcag gcttattttc ataaaacaca ttaacgcttg        480
catttggatt agttaaacat ggcatcaaat gggaagaatc ccgaaatctc aagctgttct        540
cattggaccg cagcactcca gaattcaagt ctcttgacca tacttttttt tgcctgctat        600
caacagtaaa attttgagct ttaccatatc cacagtcaag tggctcattt cgagagttac        660
gcttcctcct cattaaatca cktacagaac ggccttccct ggagttatgt gtgcctgtac        720
ctgcatttcg taatgtaaca tccacctgcc ctccatcttc acttgaaaag caactaatga        780
actcagaatc tttggtcgaa cttgtccata tgtcaggcct gcaagaattg acacacgtcg        840
aatctgtatt cactttctca gcctcatgaa aaggtaaaga tccccaaaat gatttctctt        900
tcttgtgact gcaagaacct gaatcaatgc catgcaataa tattgcaagt ttggaagatc        960
tttcattctc aacattaaga tctctatcag gtgagttttc agtcgaccct ccagaagaag       1020
agaacatatc atctgcakgt acgcagt                                          1047
```

SEQ ID NO 6: Sequence of the ToLCNDV resistant donor plant comprising SNP_06.
(forward strand in reference genome)

```
                                                                   SEQ ID NO: 6
gcgtacmtgc aggcaaagaa tggcacagta cagtaatggt agctcatctg ttcatcaagg         60
agaatcaagc tgcctcagcc attcagtatc ggttccaccc ctgatcatct cctacaatga       120
tcgcattcgt cctctccttg atgctgttga caagcttcgt cacctcatga tcatgagaga       180
aggcatccaa ctgcctacca tagttgttgt tggtgatcag tcawccggta agtcaagtgt       240
```

-continued

```
cctcgagtcg ttggctggga tcagcctacc tcgaggtcag ggcatctgca ccagggtccc      300
tctgataatg aggctccaaa accatcctga tcccgaaccc gagcttgttt tggagtacaa      360
tgggaaaaag atccacaccg acgaatcctt cattgctgaa gacatctgta cagctacaga      420
ggagattgct ggcagtggca aagga atatc gaaagcgcca ttgactttga ttgtgaagaa     480
aaatggtgtt cctgatctta caatggttga tctccctgga attacragag tgcctgttaa     540
agatcagcct gaagacattt atgaccaaat aaaagatata atcatggaac atatcaagcc     600
agaagagagc atcatcttga atgtcttgtc tgcgacggtt gattttccaa cttgtgaatc     660
gatacggatg tctcaaagtg tcgacaagac gggaatgaga acgttggcag ttgtgactaa     720
gtctgacaag gcaccagaag gcctacacga aaggtcacc rcggatgatg tcagtatcgg      780
ccttggttat gtttgcgtta ggaaccgaat tggcaatgag acatatgagg aagctcgggt     840
tgcagaagcc aaattgtttt caactcatcc tcttctctcc aaaattgaca aatctgttgt     900
gggcattcca gtcttggctc agaagttggt gcaaattcaa gcaggtaccc aaactaattc     960
ctgactcaaa agctaggttc cgttagataa ccattttgtt ttagaaaatc aagtttattt    1020 tctctaaaatm gtgtaccatg attttcatct ttcttaaata aaaaagttgm attcttwact   1080
aaattttaaa agcaaaaaca agttttaata ctttttttt                           1118
```

SEQ ID NO 7: KASP-assay primer for FAM allele of SNP_01.

SEQ ID NO 8: KASP-assay primer for VIC allele of SNP_01.

SEQ ID NO 9: KASP-assay common primer for SNP_01.

SEQ ID NO 10: KASP-assay primer for FAM allele of SNP_02.

SEQ ID NO 11: KASP-assay primer for VIC allele of SNP_02.

SEQ ID NO 12: KASP-assay common primer for SNP_02.

SEQ ID NO 13: KASP-assay primer for FAM allele of SNP_03.

SEQ ID NO 14: KASP-assay primer for VIC allele of SNP_03.

SEQ ID NO 15: KASP-assay common primer for SNP_03.

SEQ ID NO 16: KASP-assay primer for FAM allele of SNP_04.

SEQ ID NO 17: KASP-assay primer for VIC allele of SNP_04.

SEQ ID NO 18: KASP-assay common primer for SNP_04.

SEQ ID NO 19: KASP-assay primer for FAM allele of SNP_05.

SEQ ID NO 20: KASP-assay primer for VIC allele of SNP_05.

SEQ ID NO 21: KASP-assay common primer for SNP_05.

SEQ ID NO 22: KASP-assay primer for FAM allele of SNP_06.

SEQ ID NO 23: KASP-assay primer for VIC allele of SNP_06.

SEQ ID NO 24: KASP-assay common primer for SNP_06.

SEQ ID NO 25: Sequence of the ToLCNDV resistant donor plant comprising
SNP_07 (reverse strand in reference genome).
CACTATAAACCTTATTCTTTTTAAGAAATCATGTTTCAAACCCAATAAAAG

TAAGTTGATACATTGTCCTTGTAGAAATTGTCAAAACTAAATACAGTAA C AAAC

AACTTTAAAATTTTGTATCATGTTATATTACAATATGGCCCATCTCACGTTTTCCC

AATTGTCTTGAGAATTCAATGATATTTCATTCCAATATAA

-continued

SEQ ID NO: 26: Sequence of the ToLCNDV resistant donor plant comprising
SNP_08 (reverse strand in reference genome)
TCTCATTTTCAATGCCATGTTTTTTTTACTCATTTATCAACGAGCACACTGT

ACAATTTTTAAGATCCATTCTCTCTCAAGATGCCATTTAATTGTGTG[G]CATCATT

CTTTAATTTTGATATGATTATGTACTTGACAACAGGAGGGAGGCTGATCTTATTT

GAGATCTTGTTAAAGAAGTGTTATCTACAATAAATCGC

SEQ ID NO 27: KASP-assay primer for FAM allele of SNP_07

SEQ ID NO 28: KASP-assay primer for VIC allele of SNP_07

SEQ ID NO 29: KASP-assay common primer for SNP_07

SEQ ID NO 30: KASP-assay primer for FAM allele of SNP_08

SEQ ID NO 31: KASP-assay primer for VIC allele of SNP_08

SEQ ID NO 32: KASP-assay common primer for SNP_08

GENERAL METHODS

Figure 1:
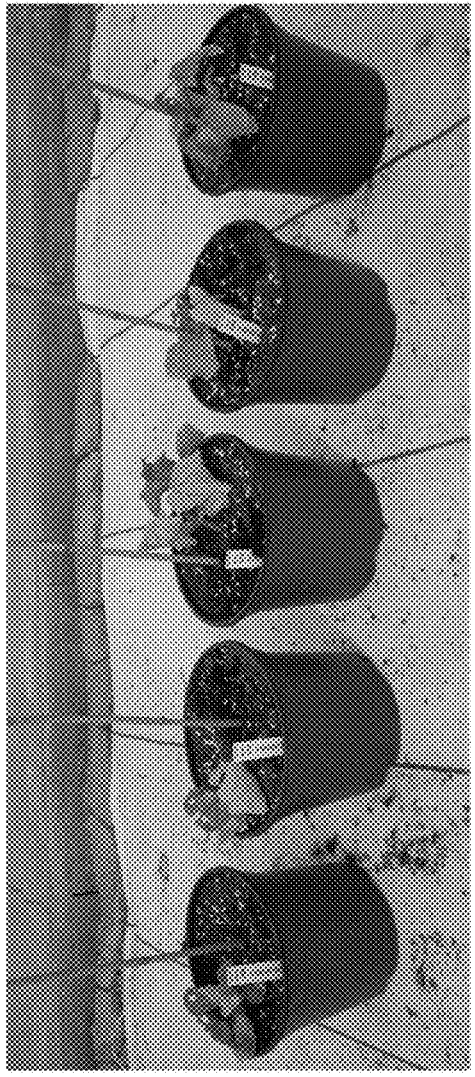
FIG. 1: Shown is a ToLCNDV sensitive recurrent plant (upper picture) and a recurrent plant into which ToLCNDV resistance was integrated (lower picture) by introgression of a fragment comprising the sequence of the donor in-between SNP_01 and SNP_06. The picture was taken 25 days post infection (dpi) with ToLCNDV by whitefly transmission.
Figure 1:
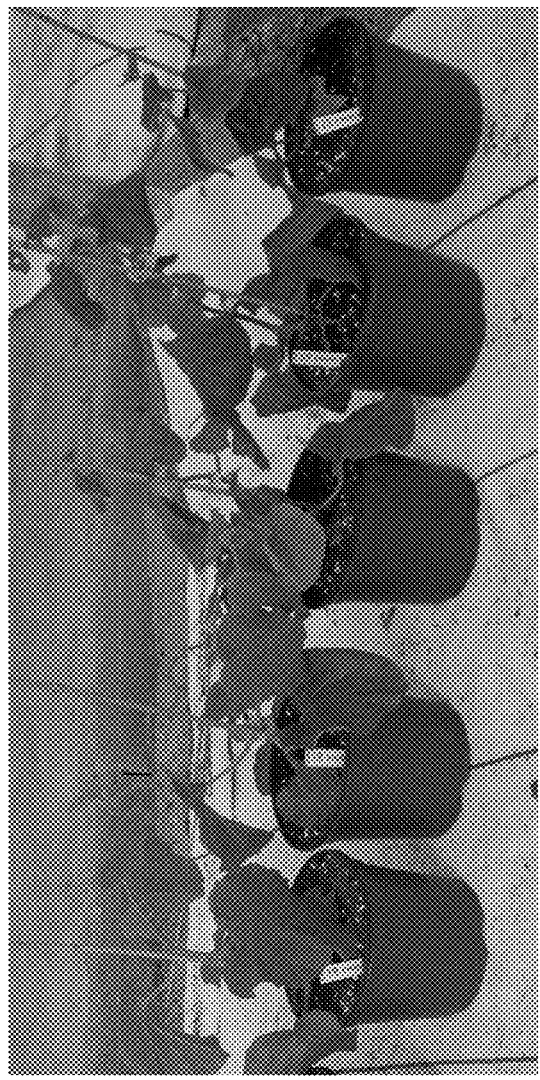

1. Determination of Symptom Level on ToLCNDV Infected Plants 1.1 Plants and Pathogens (Virus)

A melon plant (*Cucumis melo*) infecting strain of ToLCNDV is used for infection of melon plants. In the present invention a ToLCNDV strain isolated in Murcia, Spain was used as inoculum.

1.2 ToLCNDV Propagation

The ToLCNDV inoculum source is maintained on living infected melon plants. It must be ensured, that pure virus isolates are used and that neither the virus source, nor the whiteflies are contaminated with other diseases, in particular with other viruses (e.g. CGMMV, CYSDV, CYVY SqMV). For pre-multiplication of the ToLCNDV inoculum whiteflies (*Bemisia tabaci*) are fed on ToLCNDV sensitive (susceptible), infected melon plants in an insect proven cage. Before infection of test plants, put ToLCNDV infected plants into an insect proven cage, release whiteflies to the same cage and allow the whiteflies to feed for approximately 3 days on the ToLCNDV infected plants.

1.3 Inoculation of Plants to be Tested

For each genotype of melon plants to be analysed 14 plants were grown until the first true leaf is expanded (normally 12-15 days after sowing), 12 of which were infected and 2 were mock infected. Also 12 plants of susceptible varieties were included, in this experiment variety Gandalf F1 (Hild Samen) and variety Vedantrais. The 12 plants per genotype to be tested on ToLCNDV resistance were put into an insect proof cage, infected whiteflies obtained as described under 1.2 above, were released into the cage to infect the plants. It has to be ensured that at least 5-10 whiteflies are available for each test plant in the cage. Whiteflies and test plants are kept in the cage for approximately 48 hours, before the whiteflies are eliminated with an appropriate insecticide. Also two plants per genotype were mock infected, i.e. they were treated in the same manner as the test plants apart from that the whiteflies used for infection were free of ToLCNDV.

1.4 Growing Infected Test Plants

Infected test plants obtained as described under 1.3 were transplanted to bigger pots, transferred into a greenhouse with cooling equipment. The plants were grown at approximately 18° C. night temperature and approximately 25° C. day temperature in a timeframe of 14 to 16 hours daylight. The infected plants for each infected genotype were grown in two replicates in two different plots, each of which comprises 6 ToLCNDV infected plants and 1 mock infected plant. The plots are randomized in respect to the growing area.

1.5. Scoring the Symptom Level of ToLCNDV Infection

The scoring of the symptom level may already be done approximately 15 days post infection (dpi) with ToLCNDV but is preferably done approximately 30 days post infection (dpi) with ToLCNDV, or later. In case plants are present which show recovery from the virus infection, a further scoring of the symptom is done approximately 45 days post infection (dpi) with ToLCNDV.

The following symptom levels are to be used according to the phenotypes indicated in the following:

| Symptom level | Observed phenotype |
|---|---|
| 1 | Dead plant |
| 2 | Severe mosaic and curling, chlorosis and growth reduction. No recovery |
| 3 | Strong mosaic and curling, chlorosis and growth reduction. No recovery |
| 4 | Curling and mosaic, chlorosis, no or mild growth reduction. No recovery |
| 5 | Curling and mosaic, chlorosis, no growth reduction. Slight recovery of the upper plant zone |
| 6 | Mild curling, mosaic and chlorosis, no growth reduction. Recovery of the upper middle plant |

| Symptom level | Observed phenotype |
|---|---|
| 7 | Mild curling, mosaic and chlorosis, no growth reduction. Symptoms appear only in the lower plant zone |
| 8 | Faint mosaic |
| 9 | No symptoms |

1.6 Optional Additional Tests

It is recommended to use at least one genotype highly resistant to ToLCNDV (symptom level 8-9) and one genotype highly sensitive to ToLCNDV (symptom level 1) in each experimental setup. It is further recommended to also include a genotype being intermediate resistant to ToLCNDV infection in each test setup. Best results are obtained when the just mentioned genotypes are included and the symptom levels of each genotype is scored relative to the results obtained for the highly resistant, highly sensitive and intermediate resistant genotypes. These genotypes also give a clear indication on the amount of infection of melon plants with ToLCNDV by the whiteflies.

Furthermore, it is advisable to check infection and spreading of ToLCNDV in infected plants and control plants. This can be done by checking for the presence and amount of virus DNA in upper parts of the plants. A suitable way to check for the presence and amount of ToLCNDV DNA in upper plant parts is hybridization of plant material with a probe hybridizing with the DNA of the ToLCNDV strain used. Various hybridization techniques are well known in the art. A simple so called Dot Blot analysis is sufficient for obtaining valuable results. Likewise PCR or quantitative PCR techniques can be used.

EXAMPLES

1. Selection of ToLCNDV Resistant Donor Plants

The symptom level of wild accessions of melon plants were tested for ToLCNDV resistance according to the test described under "General Methods". A wild donor plant was identified which has a high resistance to ToLCNDV infection, having a resistance level of about 7 (as seen further below the average disease score was 7.4, while the susceptible plant had an average score of 2.0).

2. Identification of Genomic Location of ToLCNDV Resistance

Three mapping populations were developed including the use of the donor plant obtained in Example 1 to map the position of the ToLCNDV resistance conferring fragment (QTL) in the genome of donor melon plant.

Analysis in these mapping populations revealed one major QTL associated with resistance, located on chromosome 5 and showing dominant inheritance patterns.

The magnitude of the detected fragment QTL and observed inheritance patterns suggested a single locus dominant gene. From resistant material the inventors developed BC (back cross) lines to fine map and further investigate resistance from the donor. Genotypic results in 10 advanced BC families developed through phenotypic selection showed >93% agreement with individual phenotypes.

The markers identified during fine mapping and their respective positions according to publicly known data from Diaz et al. (2015, Mol Breeding 35, 188) is shown in the following Table:

| SNP | Marker ID | | SNP position | Pseudo-molecule coordinates |
|---|---|---|---|---|
| | AI_13-H12 | CM3.5_scaffold00003 | 7996720 | 27276249 |
| SNP_01 | mME11320_k | CM3.5_scaffold00003 | 7824960 | |
| SNP_02 | mME43070_k | CM3.5_scaffold00003 | 6950286 | |
| SNP_03 | mME10621_k | CM3.5_scaffold00003 | 6553350 | |
| SNP_04 | mME50729_k | CM3.5_scaffold00003 | 5785550 | |
| SNP_05 | mME32395_k | CM3.5_scaffold00003 | 5202092 | |
| | CMGAAN144 | CM3.5_scaffold00003 | 5123876 | 24403405 |
| | CMPSNP682 | CM3.5_scaffold00009 | 4703882 | 15854444 |
| SNP_06 | mME49184_k | CM3.5_scaffold00009 | 2607437 | |
| | CMPSNP460 | CM3.5_scaffold00009 | 1816109 | 12966671 |

3. Development of KASP-Assay

A KASP-assay was developed for identifying the SNPs flanking the QTL. The SNPs associated with the QTL can be determined by use of the following primers in a KASP-assay:

| SNP | FAM allele | VIC allele | Common Primer |
|---|---|---|---|
| SNP_01 | SEQ ID NO 7 | SEQ ID NO 8 | SEQ ID NO 9 |
| SNP_02 | SEQ ID NO 10 | SEQ ID NO 11 | SEQ ID NO 12 |
| SNP_03 | SEQ ID NO 13 | SEQ ID NO 14 | SEQ ID NO 15 |
| SNP_04 | SEQ ID NO 16 | SEQ ID NO 17 | SEQ ID NO 18 |
| SNP_05 | SEQ ID NO 19 | SEQ ID NO 20 | SEQ ID NO 21 |
| SNP_06 | SEQ ID NO 22 | SEQ ID NO 23 | SEQ ID NO 24 |

4. Introgression of ToLCNDV into a Cultivated Melon Plant

Figure 2:
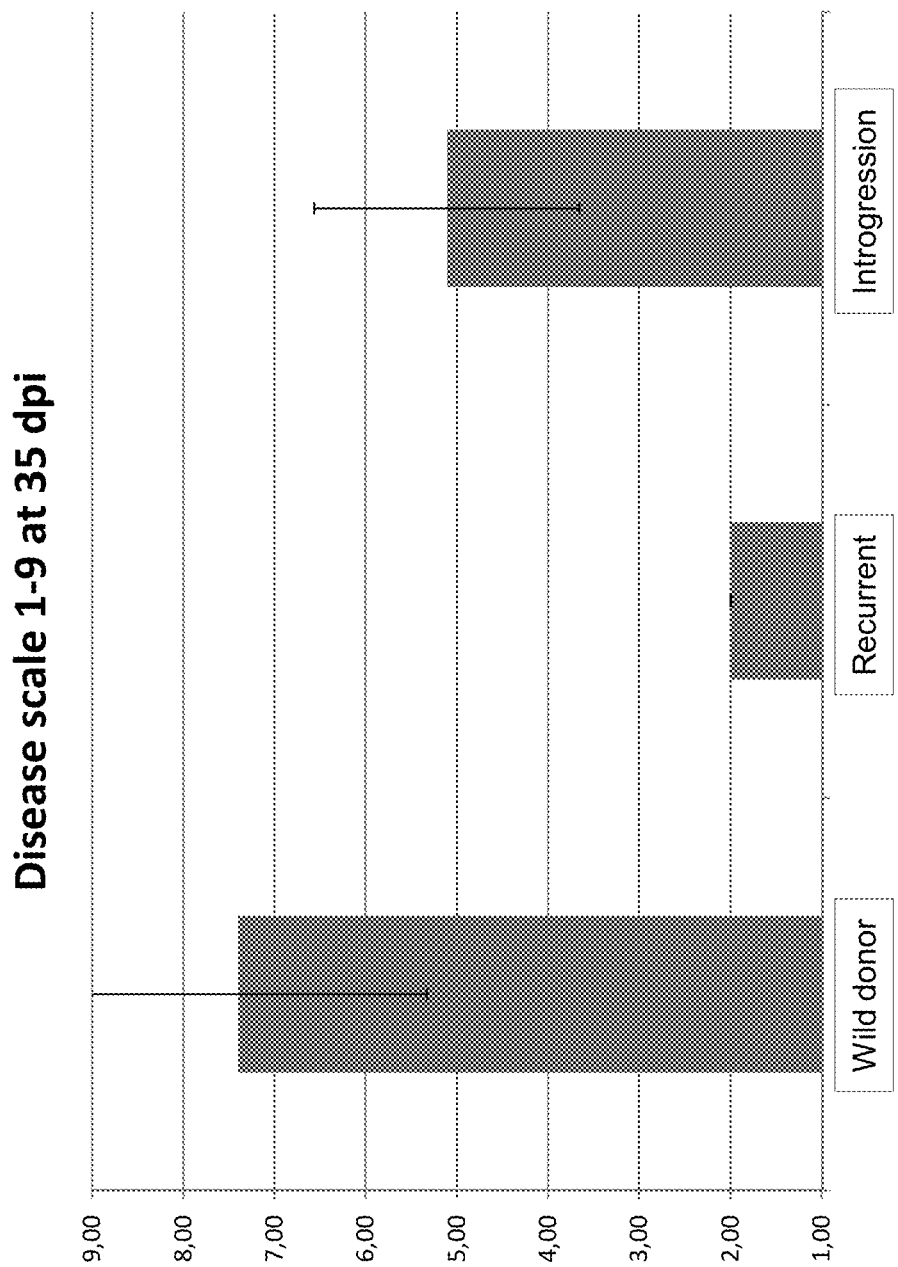
FIG. 2: Shown are the symptom levels 35 days post infection (dpi) with ToLCNDV by whitefly transmission of a donor plant being ToLCNDV resistant (Wild Donor), a recurrent plant (Recurrent) and a plant obtained after introgression of the ToLCNDV resistance from the donor plant into the recurrent plant (Introgression). The symptom levels were determined as described herein under "General Methods".

Backcrossing has been performed with cultivated melon plants and recurrent melon plants having an increased resistance to ToLCNDV have been obtained. The presence of the QTL in these lines was established by use of the KASP-assay sequences shown in Example 3. A representative result for the ToLCNDV symptom level achieved in those plants is given in the following Table and in FIG. 2. The symptom levels have been determined 35 days post infection (dpi) according to the method described herein under "General Methods".

| | AVG | STDV |
|---|---|---|
| Wild Donor | 7.40 | 2.07 |
| Recurrent | 2.00 | 0.00 |
| Introgression | 5.11 | 1.45 |

AVG: Average Value of Tested Genotype, STDV: Standard Deviation

Additional backcrossing is done to introgress the resistance in elite Piel de Sapo, Galia, Cantaloup and Charentais backgrounds. Genotypic results in 10 advanced BC families developed through phenotypic selection show >93% agreement with individual phenotypes.

5. Additional SNP Markers Closely Linked to the Resistance

Two additional markers (SNP_07 and SNP_08) were found closely linked to the resistance QTL, located in between the previous SNP_03 and SNP_04 on chromosome 5. Previously SNP_03 was found to be most closely linked to the QTL. In the further analysis SNP_08 was found most closely linked and SNP_07 was found to be closely linked and also to be unique in a large panel of melon germplasm.

TABLE 3

| Marker name | SNP marker | Strand orientation of marker sequence with respect of reference genome DHL92 v3.5.1 | SNP | SNP genotype of resistant donor (homozygous) | SNP haplotype of introgression fragment, comprising the donor nucleotide for one or more or all of the SNP markers | Position of SNP on Melon reference genome (DHL92) v3.5.1 (cucurbitgenomics.org database) |
|---|---|---|---|---|---|---|
| mME49184 | SNP_06 (nt 445 of SEQ ID NO 6) | Forward (+ strand) | A/G | AA | A | 13758001 |
| mME32395 | SNP_05 (nt 839 of SEQ ID NO 5) | Reverse (– strand) | C/T | CC (GG when referring to forward strand) | C (G when referring to forward strand) | 24481621 |
| mME50729 | SNP_04 (nt 227 of SEQ ID NO 4) | Forward (+ strand) | A/G | AA | A | 25065080 |
| mME72209 | SNP_08 (nt 101 of SEQ ID NO: 26) | Reverse (– strand) | A/G | GG (CC when referring to forward strand) | G (C when referring to forward strand) | 25257353 |
| mME72207 | SNP_07 (nt 101 of SEQ ID NO: 25) | Reverse (– strand) | C/T | CC (GG when referring to forward strand) | C (G when referring to forward strand) | 25361598 |
| mME10621 | SNP_03 (nt 68 of SEQ ID NO 3) | Forward (+ strand) | C/T | TT | T | 25832880 |
| mME43070 | SNP_02 (nt 945 of SEQ ID NO 2) | Forward (+ strand) | G/T | TT | T | 26229815 |
| mME11320 | SNP_01 (nt 101 of SEQ ID NO 1) | Reverse (– strand) | C/T | CC (GG when referring to forward strand) | C (G when referring to forward strand) | 27104489 |

It is noted that the DNA sequences for SNP_01, SNP_05, SNP_07 and SNP_08 are the reverse strand (– strand) with respect of the reference genome sequence found on the world wide web at cucurbitgenomics.org for melon (DHL92) v3.5.1. This can be seen by Blast analysis of the sequence against the reference genome database, resulting in an alignment with either the forward strand (wherein nucleotide numbering is counting upwards) or with the reverse strand/complement strand whereby nucleotide numbering is counting downwards. It is understood that this is just a matter of naming. So a nucleotide C for SNP_01 at nucleotide 101 in SEQ ID NO: 1 corresponds to the nucleotide G for SNP_01 at nucleotide 101 of the complementary sequence of SEQ ID NO: 1. When referring to the donor SNP nucleotide in a reverse strand sequence, such reference thus also comprises a reference to the complement donor SNP nucleotide in the complement/forward strand of the sequence (and vice versa, reference to a donor nucleotide in a forward strand sequence can also be referred to by referring to the complement donor nucleotide in the reverse strand).

It is also noted that for SEQ ID NO: 26, when BLAST analysis against the database of the reference genome Melon (DHL92) v3.5.1 (world wide web at cucurbitgenomics.org) is done, shows that in this reference genome there are 10 additional nucleotides inserted between nucleotide 27 and 28 of SEQ ID NO: 26. There is, therefore, only a sequence identity of 94.79% given between SEQ ID NO: 26 and the reference genome region. However, an 'A' is present in the reference genome at the SNP position corresponding to nucleotide 101 of SEQ ID NO: 26 (which is a 'G').

The donor nucleotide of any of the SNP markers herein may thus be present in the SEQ ID NO: mentioned, or at the corresponding nucleotide of a sequence comprising at least 94% (or at least 95%, 96%, 97%, 98%, 99%) sequence identity to the given sequence. This applies to all SNP markers. The 'corresponding nucleotide' can be easily identified by pairwise alignment using e.g. Emboss-Needle pairwise alignment (using default parameters).

The above SNP markers, including markers SNP_07 (mME72207) and SNP_08 (mME72209), were analyzed in a KASP assay (provided below) for 210 diverse melon material. The donor SNP nucleotide for SNP_07 (mME72207), i.e. a 'C' at nucleotide 101 of SEQ ID NO: 25 (corresponding to a G at nucleotide 101 of the strand complementary to SEQ ID NO: 25) was unique to the donor and not found in any of the other melon accessions analyzed.

SNP_08 (mME72209) had the best correlation to the phenotype in the mapping population.

A KASP-assay was developed for identifying the SNPs flanking the QTL. The SNPs associated with the QTL can be determined by use of the following primers in a KASP-assay:

| SNP | FAM allele | VIC allele | Common Primer |
|---|---|---|---|
| SNP_07 | SEQ ID NO: 27 | SEQ ID NO: 28 | SEQ ID NO: 29 |
| SNP_08 | SEQ ID NO: 30 | SEQ ID NO: 31 | SEQ ID NO: 32 |

A total of 210 diverse melon lines, accessions and varieties were analyzed in a KASP assay for SNP_01 to SNP_06. Below the SNP haplotype for some of the material is given. It is noted that for SNP_01, SNP_05, SNP_07 and SNP_08, the assay was based on detection of the SNP nucleotide in the reverse strand, which was converted into the SNP nucleotide in the complementary (forward) strand in the data presented below.

| SNP Haplotype of ToLCNDV donor | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| SNP_06 | A | A | A | G | G | A | A | A | A | G | A | A | G | A | A | G |
| SNP_05 | G | A | A | G | A | A | G | A | A | G | G | A | G | A | G | G |
| SNP_04 | A | A | A | A | A | A | A | A | A | A | A | A | A | A | G | A |
| SNP_08 | C | C | C | C | T | T | T | T | T | T | T | T | T | T | T | T |
| SNP_07 | G | A | A | A | A | A | A | A | A | A | A | A | A | A | A | A |
| SNP_03 | T | C | C | T | C | C | C | T | T | T | T | T | T | T | C | T |
| SNP_02 | T | G | T | G | T | T | T | G | T | T | G | G | G | T | G | T |
| SNP_01 | G | A | A | G | G | A | A | G | A | G | A | A | G | G | A | G |

SNP_07 and/or SNP_08 are markers closely linked to the QTL and can be used to detect the introgression fragment comprising the QTL and comprising the donor nucleotide for SNP_07 and/or SNP_08, or other applications described herein.

The invention claimed is:

1. A cultivated melon plant cell of the species *Cucumis melo* comprising an introgression fragment from chromosome 5 of a ToLCNDV resistant donor plant, wherein the introgression fragment confers ToLCNDV resistance and comprises a Cytosine (C) for SNP_07 at nucleotide 101 of SEQ ID NO: 25, or at the equivalent nucleotide of a sequence comprising at least 94% sequence identity to SEQ ID NO: 25, and/or a Guanine (G) for SNP_08 at nucleotide 101 of SEQ ID NO: 26, or at the equivalent nucleotide of a sequence comprising at least 94% sequence identity to SEQ ID NO: 26, and wherein the introgression fragment is obtainable from seeds, a representative sample of which has been deposited under accession number NCIMB 42585.

2. The cultivated melon plant cell of claim 1, wherein the introgression fragment comprises the sequence of the ToLCNDV resistant donor melon plant in-between nucleotide 25832880 and nucleotide 25065080 of chromosome 5, and wherein the introgression fragment is obtainable from seeds, a representative sample of which has been deposited under accession number NCIMB 42585.

3. The cultivated melon plant cell according to claim 1, wherein the introgression fragment comprises a Cytosine (C) for SNP_07 at nucleotide 25361598 of chromosome 5 and/or a Guanine (G) for SNP_08 at nucleotide 25257353 of chromosome 5.

4. The cultivated melon plant cell according to claim 1, comprising the introgression fragment in homozygous form and comprising the genotype CC for SNP_07 and/or the genotype GG for SNP_08.

5. The cultivated melon plant cell according to claim 1, wherein the introgression fragment further comprises a Thymine (T) for SNP_03 at nucleotide 68 of SEQ ID NO: 3 or at the equivalent nucleotide of a sequence comprising at least 94% sequence identity to SEQ ID NO: 3 and/or a Adenine (A) for SNP_04 at nucleotide 227 of SEQ ID NO: 4 or at the equivalent nucleotide of a sequence comprising at least 94% sequence identity to SEQ ID NO: 4.

6. A cultivated melon plant comprising melon plant cells according to claim 1.

7. A cultivated melon seed comprising plant cells according to claim 1.

8. A cultivated melon fruit comprising plant cells according to claim 1.

9. Cultivated melon plant propagation material comprising plant cells according to claim 1.

10. A method for producing a ToLCNDV resistant melon plant comprising the following steps
   a) selecting a ToLCNDV resistant donor plant comprising a Cytosine (C) for SNP_07 at nucleotide 101 of SEQ ID NO: 25, or at the equivalent nucleotide of a sequence comprising at least 94% sequence identity to SEQ ID NO: 25, and/or a Guanine (G) for SNP_08 at nucleotide 101 of SEQ ID NO: 26, or at the equivalent nucleotide of a sequence comprising at least 94% sequence identity to SEQ ID NO: 26,
   b) crossing the donor plant selected in step a) with a plant sensitive to ToLCNDV,
   c) obtaining seeds from the plants crossed in step b), and optionally
   d) verifying if the plants grown from the seeds obtained in step c) are resistant to ToLCNDV and/or comprise a Cytosine (C) for SNP_07 at nucleotide 101 of SEQ ID NO: 25, or at the equivalent nucleotide of a sequence comprising at least 94% sequence identity to SEQ ID NO: 25, and/or a Guanine (G) for SNP_08 at nucleotide 101 of SEQ ID NO: 26, or at the equivalent nucleotide of a sequence comprising at least 94% sequence identity to SEQ ID NO: 26.

11. A method for producing melon seeds comprising the following steps:
   a) growing a melon plant comprising at least one chromosome 5 having an introgression fragment from chromosome 5 of a ToLCNDV resistant donor plant, wherein the introgression fragment confers ToLCNDV resistance and comprises a Cytosine (C) for SNP_07 at nucleotide 101 of SEQ ID NO: 25, or at the equivalent nucleotide of a sequence comprising at least 94% sequence identity to SEQ ID NO: 25, and/or a Guanine (G) for SNP_08 at nucleotide 101 of SEQ ID NO: 26, or at the equivalent nucleotide of a sequence comprising at least 94% sequence identity to SEQ ID NO: 26, and wherein the introgression fragment is obtainable from seeds, a representative sample of which has been deposited under accession number NCIMB 42585,
   b) harvesting the fruits of the melon plants grown in step a), and optionally
   c) collecting the seeds from the fruits obtained in step b).

12. A method for producing hybrid melon seeds comprising the following steps
   a) crossing a first inbred melon plant comprising at least one chromosome 5 having an introgression fragment from chromosome 5 of a ToLCNDV resistant donor plant, wherein the introgression fragment confers ToLCNDV resistance and comprises a Cytosine (C) for SNP_07 at nucleotide 101 of SEQ ID NO: 25, or at the equivalent nucleotide of a sequence comprising at least 94% sequence identity to SEQ ID NO: 25, and/or a Guanine (G) for SNP_08 at nucleotide 101 of SEQ ID NO: 26, or at the equivalent nucleotide of a sequence comprising at least 94% sequence identity to SEQ ID NO: 26, and wherein the introgression fragment is obtainable from seeds, a representative sample of which has been deposited under accession number NCIMB 42585,
   with a second inbred melon plant with or without a chromosome 5 having an introgression fragment from chromosome 5 of a ToLCNDV resistant donor plant, wherein the introgression fragment comprises a Cytosine (C) for SNP_07 at nucleotide 101 of SEQ ID NO: 25, or at the equivalent nucleotide of a sequence comprising at least 94% sequence identity to SEQ ID NO: 25, and/or a Guanine (G) for SNP_08 at nucleotide 101 of SEQ ID NO: 26, or at the equivalent nucleotide of a sequence comprising at least 94% sequence identity to SEQ ID NO: 26, and wherein the introgression fragment is obtainable from seeds, a representative sample of which has been deposited under accession number NCIMB 42585, and
   b) selecting seeds obtained from the cross of step a).

13. A method for producing a melon fruit comprising the following steps:
   a) growing a plant comprising at least one chromosome 5 having an introgression fragment from chromosome 5 of a ToLCNDV resistant donor plant, wherein the introgression fragment confers ToLCNDV resistance and comprises a Cytosine (C) for SNP_07 at nucleotide 101 of SEQ ID NO: 25, or at the equivalent nucleotide of a sequence comprising at least 94% sequence identity to SEQ ID NO: 25, and/or a Guanine (G) for SNP_08 at nucleotide 101 of SEQ ID NO: 26, or at the equivalent nucleotide of a sequence comprising at least 94% sequence identity to SEQ ID NO: 26, and wherein the introgression fragment is obtainable from seeds, a representative sample of which has been deposited under accession number NCIMB 42585, and
   b) harvesting the fruits produced by the plants grown in step a).

* * * * *

```
                        SEQUENCE LISTING

<160> NUMBER OF SEQ ID NOS: 32

<210> SEQ ID NO 1
<211> LENGTH: 200
<212> TYPE: DNA
<213> ORGANISM: Cucumis melo

<400> SEQUENCE: 1
agctggtgca aagctggcat tcaaatcgaa tgaagaaata gcagtacaag tgaagtcaat      60
tccactagat gaagtaatcc cggattcaga acgagtgctt ctaataaaaa tcgatgttca     120
aggctgggaa tatcatgtgc taaaaggggc aaagagaatt ttgtcaagga agggcactga     180
agctccatat ctcatctatg                                                 200

<210> SEQ ID NO 2
<211> LENGTH: 1145
<212> TYPE: DNA
<213> ORGANISM: Cucumis melo

<400> SEQUENCE: 2
ttgtaatcat ggccattgcc tgatytgcag aatgtggcgt cttgattggg cacggtctgg      60
atgaagttac tccaaagctt gtggaagtta atgggttctt ctcttcaccr tctgrtctcc     120
ttcccatcga caatgtggtt tcttcttcaa acacaaaaga aaccctgtt gaagctgtag      180 aagaaagctg tgagttcttt tctccactca gttctaggtt tagttttta tttgttttt      240 ttttcttttt tccttttac ttgctttgag ctgtaggaca caacacaaaa tgataagaac      300
aaaaatcaat ctatgttatt gttgtcattg tctcgcctgc ctcttcaagg taactaggct     360
ataacactga tccaaaatgt ataatcttta ttgctaagta acttatattg caaagattgg     420
gatggaatag gagcataggt tgcatctaat agttttgtcc aactttggtt atagtttcag     480
ccagtttgtt cagatgaaat tcttagtgat tatcactaat ggaattgttt ttataaatgt     540
tgtaggtgtt gaaagaagtg aagaatatga aaggaaagc aggggaaccg agaaggctga      600
aatcttaccg acaaaagcaa catctgaagc aggttctgaa gtccaacctg tttccagtga     660
ttctgctcag atggtaccca atatgttgga gctcggtgat gcttataagc tagctgtagg     720
tgctagagga ggaagacaat tgtctggcaa gcttttggaa caatggatyg ggaaggaatc     780
ttcaaaagtt agtgaagatc tgaagcttct cttgacacaa ctctcattta atcgtttgaa     840
tgaccaatca cgggagatga gtccaaggct gtccgtaaat ggagacgagg tgaggaactt     900
tgattacttg agygctgttg ggatgcaaat gctacaaaaa aggwtttcgc ttgaaagaaa     960
```

```
tgagtccggt gtagaatctt tagatggaag cataattagt gaaatcgatg gggaaaacat      1020
ggctgatagg ttgaaacgac agattgagta tgataagaag gttmtgartt ctttatacaa      1080
ggaattggag gaagaaagaa atgcatccgc aattgctgca atcaggcaa tggccatgat       1140 tacaa                                                                  1145
```

<210> SEQ ID NO 3
<211> LENGTH: 168
<212> TYPE: DNA
<213> ORGANISM: Cucumis melo

<400> SEQUENCE: 3

```
agacggcgta catgcagcat tctgttaccc cgcgatgccc agcgatgaaa caactccttt        60
gcatccttat ggtccagagg ttccagatca tacgactcac caaatgcagg aaacttaaat       120
ctagaggtga ccaaaatttt gcagttgggt aatcgggaga acttttca                    168
```

<210> SEQ ID NO 4
<211> LENGTH: 468
<212> TYPE: DNA
<213> ORGANISM: Cucumis melo

<400> SEQUENCE: 4

```
ggagkcttca tccgtcttta ccttcctcac ttttttacct aaccaagtta cgtcttgtag        60
gttgcaagat aacaaatttg gatttcttag aaacaattgt ttatgttgcc ccttcrttga       120
aagagttgga cttgtccgaa acaacttttt gtagamtacc ctcrtgtatt attaatttta      180
aatccctgaa atatctttat acaatggatt gtgagttgct ygaagaaatt tcaaaggttc      240
cagaaggtgt aatttgtacg agtgccgcag gatgcaaatc attggctaga tttcccgaca      300
acttagctga tttcatatct tgtggtaatt ctgcggtgcg taccatatct ctttctcatg      360
acttcaccat tatctctagc tcatgtatat ttaatttcat tcatataata tatattactt      420
ataactattt actgatctca tggtgcagga atgttgtaaa ggtggatg                    468
```

<210> SEQ ID NO 5
<211> LENGTH: 1047
<212> TYPE: DNA
<213> ORGANISM: Cucumis melo

<400> SEQUENCE: 5

```
tgcaggtagt caaccaatt gataatattt gctcaccatc aaaattggta accatagaca        60
tagaytgacc aagcccaggc aaaacggcat catctttttg ttttctatca ttactattct      120
gattacccaa agaaatctt cttttgtac ttggagagaa ataatccccg tctgcacatt        180
gcatggaagg tgtgctgtca tgagcatcag cattacacac accagaatta gatttcttgc      240
tagccaagat ttcacaacca ccaagagaag caggacctac gcctggggtc tctgcctyag      300
aaagccaags atcaaagcac acttgtgaag gacctgaaac tgtctcagat ccagggattt      360
ctcctacatt gggtaagcta gcctgttcaa agccatcaca cacatctaca agcggcagtc      420
taccatacat ggaactatta gaataagcag gcttattttc ataaaacaca ttaacgcttg      480
catttggatt agttaaacat ggcatcaaat gggaagaatc ccgaaatctc aagctgttct      540
cattggaccg cagcactcca gaattcaagt ctcttgacca tacttttttt tgcctgctat      600
caacagtaaa attttgagct ttaccatatc cacagtcaag tggctcattt cgagagttac      660
gcttcctcct cattaaatca cktacagaac ggccttccct ggagttatgt gtgcctgtac      720
```

```
ctgcatttcg taatgtaaca tccacctgcc ctccatcttc acttgaaaag caactaatga    780
actcagaatc tttggtcgaa cttgtccata tgtcaggcct gcaagaattg acacacgtcg    840
aatctgtatt cactttctca gcctcatgaa aggtaaaga tccccaaaat gatttctctt    900
tcttgtgact gcaagaacct gaatcaatgc catgcaataa tattgcaagt ttggaagatc    960
tttcattctc aacattaaga tctctatcag gtgagttttc agtcgaccct ccagaagaag   1020
agaacatatc atctgcakgt acgcagt                                       1047
```

<210> SEQ ID NO 6
<211> LENGTH: 1118
<212> TYPE: DNA
<213> ORGANISM: Cucumis melo

<400> SEQUENCE: 6

```
gcgtacmtgc aggcaaagaa tggcacagta cagtaatggt agctcatctg ttcatcaagg     60
agaatcaagc tgcctcagcc attcagtatc ggttccaccc ctgatcatct cctacaatga    120
tcgcattcgt cctctccttg atgctgttga caagcttcgt cacctcatga tcatgagaga    180
aggcatccaa ctgcctacca tagttgttgt tggtgatcag tcawccggta agtcaagtgt    240
cctcgagtcg ttggctggga tcagcctacc tcgaggtcag ggcatctgca ccagggtccc    300
tctgataatg aggctccaaa accatcctga tcccgaaccc gagcttgttt tggagtacaa    360
tgggaaaaag atccacaccg acgaatcctt cattgctgaa gacatctgta cagctacaga    420
ggagattgct ggcagtggca aaggaatatc gaaagcgcca ttgactttga ttgtgaagaa    480
aaatggtgtt cctgatctta caatggttga tctccctgga attacragag tgcctgttaa    540
agatcagcct gaagacattt atgaccaaat aaaagatata atcatggaac atatcaagcc    600
agaagagagc atcatcttga atgtcttgtc tgcgacggtt gattttccaa cttgtgaatc    660
gatacggatg tctcaaagtg tcgacaagac gggaatgaga acgttggcag ttgtgactaa    720
gtctgacaag gcaccagaag gcctacacga aaggtcacc rcggatgatg tcagtatcgg    780
ccttggttat gtttgcgtta ggaaccgaat tggcaatgag acatatgagg aagctcgggt    840
tgcagaagcc aaattgtttt caactcatcc tcttctctcc aaaattgaca aatctgttgt    900
gggcattcca gtcttggctc agaagttggt gcaaattcaa gcaggtaccc aaactaattc    960
ctgactcaaa agctaggttc cgttagataa ccatttgtt ttagaaaatc aagtttattt   1020
tctctaaatm gtgtaccatg attttcatct ttcttaaata aaaagttgm attcttwact   1080 aaatttaaa agcaaaaaca agttttaata cttttttt                           1118
```

<210> SEQ ID NO 7
<211> LENGTH: 43
<212> TYPE: DNA
<213> ORGANISM: Artificial Sequence
<220> FEATURE:
<223> OTHER INFORMATION: KASP-assay FAM SNP_01

<400> SEQUENCE: 7

```
gaaggtgacc aagttcatgc tccggattca gaacgagtgc ttc                       43
```

<210> SEQ ID NO 8
<211> LENGTH: 44
<212> TYPE: DNA
<213> ORGANISM: Artificial Sequence
<220> FEATURE:
<223> OTHER INFORMATION: KASP-assay VIC SNP_01

-continued

<400> SEQUENCE: 8
gaaggtcgga gtcaacggat tcccggattc agaacgagtg cttt    44

<210> SEQ ID NO 9
<211> LENGTH: 29
<212> TYPE: DNA
<213> ORGANISM: Artificial Sequence
<220> FEATURE:
<223> OTHER INFORMATION: KASP-assay common primer SNP_01

<400> SEQUENCE: 9
atgatattcc cagccttgaa catcgattt    29

<210> SEQ ID NO 10
<211> LENGTH: 45
<212> TYPE: DNA
<213> ORGANISM: Artificial Sequence
<220> FEATURE:
<223> OTHER INFORMATION: KASP-assay FAM SNP_02

<400> SEQUENCE: 10
gaaggtgacc aagttcatgc tcggactcat ttctttcaag cgaac    45

<210> SEQ ID NO 11
<211> LENGTH: 46
<212> TYPE: DNA
<213> ORGANISM: Artificial Sequence
<220> FEATURE:
<223> OTHER INFORMATION: KASP-assay VIC SNP_02

<400> SEQUENCE: 11
gaaggtcgga gtcaacggat tccggactca tttctttcaa gcgaaa    46

<210> SEQ ID NO 12
<211> LENGTH: 27
<212> TYPE: DNA
<213> ORGANISM: Artificial Sequence
<220> FEATURE:
<223> OTHER INFORMATION: KASP-assay common primer SNP_02

<400> SEQUENCE: 12
ygctgttggg atgcaaatgc tacaaaa    27

<210> SEQ ID NO 13
<211> LENGTH: 43
<212> TYPE: DNA
<213> ORGANISM: Artificial Sequence
<220> FEATURE:
<223> OTHER INFORMATION: KASP-assay FAM SNP_03

<400> SEQUENCE: 13
gaaggtgacc aagttcatgc tgatctggaa cctctggacc atg    43

<210> SEQ ID NO 14
<211> LENGTH: 45
<212> TYPE: DNA
<213> ORGANISM: Artificial Sequence
<220> FEATURE:
<223> OTHER INFORMATION: KASP-assay VIC SNP_03

<400> SEQUENCE: 14
gaaggtcgga gtcaacggat tatgatctgg aacctctgga ccata    45

<210> SEQ ID NO 15

```
<211> LENGTH: 26
<212> TYPE: DNA
<213> ORGANISM: Artificial Sequence
<220> FEATURE:
<223> OTHER INFORMATION: KASP-assay common primer SNP_03

<400> SEQUENCE: 15
ccagcgatga acaactcct ttgcat                                         26

<210> SEQ ID NO 16
<211> LENGTH: 50
<212> TYPE: DNA
<213> ORGANISM: Artificial Sequence
<220> FEATURE:
<223> OTHER INFORMATION: KASP-assay FAM SNP_04

<400> SEQUENCE: 16
gaaggtgacc aagttcatgc taaattacac cttctggaac ctttgaaatt              50

<210> SEQ ID NO 17
<211> LENGTH: 45
<212> TYPE: DNA
<213> ORGANISM: Artificial Sequence
<220> FEATURE:
<223> OTHER INFORMATION: KASP-assay VIC SNP_04

<400> SEQUENCE: 17
gaaggtcgga gtcaacggat tacaccttct ggaacctttg aaatc                    45

<210> SEQ ID NO 18
<211> LENGTH: 30
<212> TYPE: DNA
<213> ORGANISM: Artificial Sequence
<220> FEATURE:
<223> OTHER INFORMATION: KASP-assay common primer SNP_04

<400> SEQUENCE: 18
ctttatacaa tggattgtga gttgctygaa                                    30

<210> SEQ ID NO 19
<211> LENGTH: 46
<212> TYPE: DNA
<213> ORGANISM: Artificial Sequence
<220> FEATURE:
<223> OTHER INFORMATION: KASP-assay FAM SNP_05

<400> SEQUENCE: 19
gaaggtgacc aagttcatgc tggctgagaa agtgaataca gattcg                  46

<210> SEQ ID NO 20
<211> LENGTH: 47
<212> TYPE: DNA
<213> ORGANISM: Artificial Sequence
<220> FEATURE:
<223> OTHER INFORMATION: KASP-assay VIC SNP_05

<400> SEQUENCE: 20
gaaggtcgga gtcaacggat taggctgaga aagtgaatac agattca                 47

<210> SEQ ID NO 21
<211> LENGTH: 25
<212> TYPE: DNA
<213> ORGANISM: Artificial Sequence
<220> FEATURE:
<223> OTHER INFORMATION: KASP-assay common primer SNP_05
```

<400> SEQUENCE: 21
gtccatatgt caggcctgca agaat        25

<210> SEQ ID NO 22
<211> LENGTH: 48
<212> TYPE: DNA
<213> ORGANISM: Artificial Sequence
<220> FEATURE:
<223> OTHER INFORMATION: KASP-assay FAM SNP_06

<400> SEQUENCE: 22
gaaggtgacc aagttcatgc tatcaaagtc aatggcgctt tcgatatt        48

<210> SEQ ID NO 23
<211> LENGTH: 46
<212> TYPE: DNA
<213> ORGANISM: Artificial Sequence
<220> FEATURE:
<223> OTHER INFORMATION: KASP-assay VIC SNP_06

<400> SEQUENCE: 23
gaaggtcgga gtcaacggat tcaaagtcaa tggcgctttc gatatc        46

<210> SEQ ID NO 24
<211> LENGTH: 23
<212> TYPE: DNA
<213> ORGANISM: Artificial Sequence
<220> FEATURE:
<223> OTHER INFORMATION: KASP-assay common primer SNP_08

<400> SEQUENCE: 24
gaggagattg ctggcagtgg caa        23

<210> SEQ ID NO 25
<211> LENGTH: 201
<212> TYPE: DNA
<213> ORGANISM: artificial
<220> FEATURE:
<223> OTHER INFORMATION: SNP_07 at nucleotide 101

<400> SEQUENCE: 25
cactataaac cttattcttt ttaagaaatc atgtttcaaa cccaataaaa gtaagttgat        60
acattgtcct tgtagaaatt gtcaaaacta aatacagtaa caaacaactt taaaattttg        120
tatcatgtta tattacaata tggcccatct cacgttttcc caattgtctt gagaattcaa        180
tgatatttca ttccaatata a        201

<210> SEQ ID NO 26
<211> LENGTH: 201
<212> TYPE: DNA
<213> ORGANISM: artificial
<220> FEATURE:
<223> OTHER INFORMATION: SNP_08 at nucleotide 101

<400> SEQUENCE: 26
tctcattttc aatgccatgt ttttttttact catttatcaa cgagcacact gtacaatttt        60
taagatccat tctctctcaa gatgccattt aattgtgtgt gcatcattct ttaattttga        120
tatgattatg tacttgacaa caggagggag gctgatctta tttgagatct tgttaaagaa        180
gtgttatcta caataaatcg c        201

<210> SEQ ID NO 27

```
<211> LENGTH: 52
<212> TYPE: DNA
<213> ORGANISM: artificial
<220> FEATURE:
<223> OTHER INFORMATION: FAM primer for SNP_07

<400> SEQUENCE: 27
gaaggtgacc aagttcatgc ttgtagaaat tgtcaaaact aaatacagta at        52

<210> SEQ ID NO 28
<211> LENGTH: 51
<212> TYPE: DNA
<213> ORGANISM: artificial
<220> FEATURE:
<223> OTHER INFORMATION: VIC primer for SNP_07

<400> SEQUENCE: 28
gaaggtcgga gtcaacggat tgtagaaatt gtcaaaacta aatacagtaa c         51

<210> SEQ ID NO 29
<211> LENGTH: 30
<212> TYPE: DNA
<213> ORGANISM: artificial
<220> FEATURE:
<223> OTHER INFORMATION: Common primer for SNP_07

<400> SEQUENCE: 29
cgtgagatgg gccatattgt aatataacat                                 30

<210> SEQ ID NO 30
<211> LENGTH: 47
<212> TYPE: DNA
<213> ORGANISM: artificial
<220> FEATURE:
<223> OTHER INFORMATION: FAM primer for SNP_08

<400> SEQUENCE: 30
gaaggtgacc aagttcatgc tctcaagatg ccatttaatt gtgtgta              47

<210> SEQ ID NO 31
<211> LENGTH: 47
<212> TYPE: DNA
<213> ORGANISM: artificial
<220> FEATURE:
<223> OTHER INFORMATION: VIC primer for SNP_08

<400> SEQUENCE: 31
gaaggtcgga gtcaacggat tctcaagatg ccatttaatt gtgtgtg              47

<210> SEQ ID NO 32
<211> LENGTH: 29
<212> TYPE: DNA
<213> ORGANISM: artificial
<220> FEATURE:
<223> OTHER INFORMATION: Common primer for SNP_08

<400> SEQUENCE: 32
ccctcctgtt gtcaagtaca taatcatat                                  29
```